United States Patent
Beswick et al.

(10) Patent No.: US 7,131,459 B2
(45) Date of Patent: Nov. 7, 2006

(54) MULTI-PORT FLUID VALVE AND METHOD

(75) Inventors: Paul R. Beswick, Newington, NH (US); Gary A. Treadwell, Dover, NH (US)

(73) Assignee: Beswick Engineering, Inc., Greenland, NH (US)

( * ) Notice: Subject to any disclaimer, the term of this patent is extended or adjusted under 35 U.S.C. 154(b) by 0 days.

(21) Appl. No.: 10/452,621

(22) Filed: Jun. 2, 2003

(65) Prior Publication Data
US 2004/0108004 A1 Jun. 10, 2004

Related U.S. Application Data

(63) Continuation of application No. 09/513,651, filed on Feb. 25, 2000, now Pat. No. 6,725,881.

(51) Int. Cl.
*F16K 11/074* (2006.01)
(52) U.S. Cl. .................. 137/625.11; 137/635
(58) Field of Classification Search ........... 137/625.11, 137/635
See application file for complete search history.

(56) References Cited

U.S. PATENT DOCUMENTS

| | | | | |
|---|---|---|---|---|
| 878,772 | A * | 2/1908 | Clayton | 137/635 |
| 2,142,543 | A * | 1/1939 | Wheaton | 137/635 |
| 2,499,318 | A * | 2/1950 | Jungerhans | 137/635 |
| 2,609,207 | A * | 9/1952 | Van Sickle | 137/635 |
| 3,008,490 | A * | 11/1961 | Angelos | 137/625.11 |
| 3,741,248 | A * | 6/1973 | Stevens, Jr. | 137/627 |
| 4,468,017 | A * | 8/1984 | Pavone | 137/625.11 |
| 4,538,640 | A * | 9/1985 | Acker | 137/625.11 |
| 4,784,179 | A * | 11/1988 | Carbenay | 137/625.11 |
| 5,881,770 | A * | 3/1999 | Neill et al. | 137/625.11 |

* cited by examiner

*Primary Examiner*—John Rivell
(74) *Attorney, Agent, or Firm*—Lorusso & Associates

(57) ABSTRACT

A multi-port valve is disclosed having a ball bearing support system for a stator/rotor/valve stem assembly within a valve housing. Slipper seals or alternatively, poppet seals, connect a plurality of apertures situated in the rotor and a plurality of apertures situated in the adjoining stator so that a common central fluid receiving channel of the stator can be connected to a peripheral fluid delivery channel of the stator via a transfer channel in the rotor. The valve assembly provides a durable, virtually leak-proof system for delivery of a variety of fluids through the same delivery channel.

20 Claims, 38 Drawing Sheets

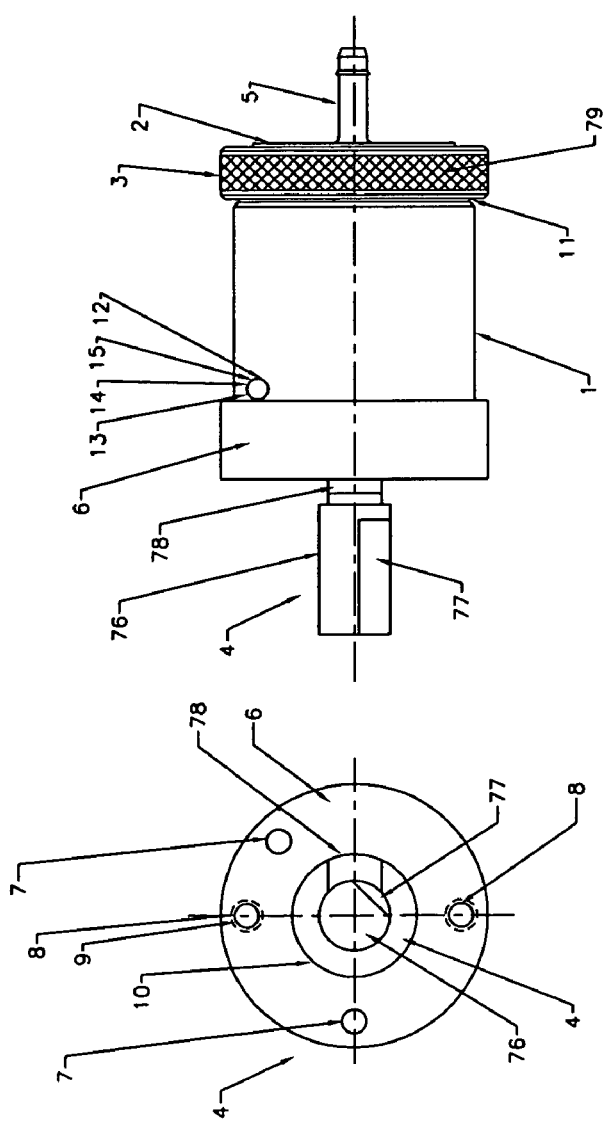

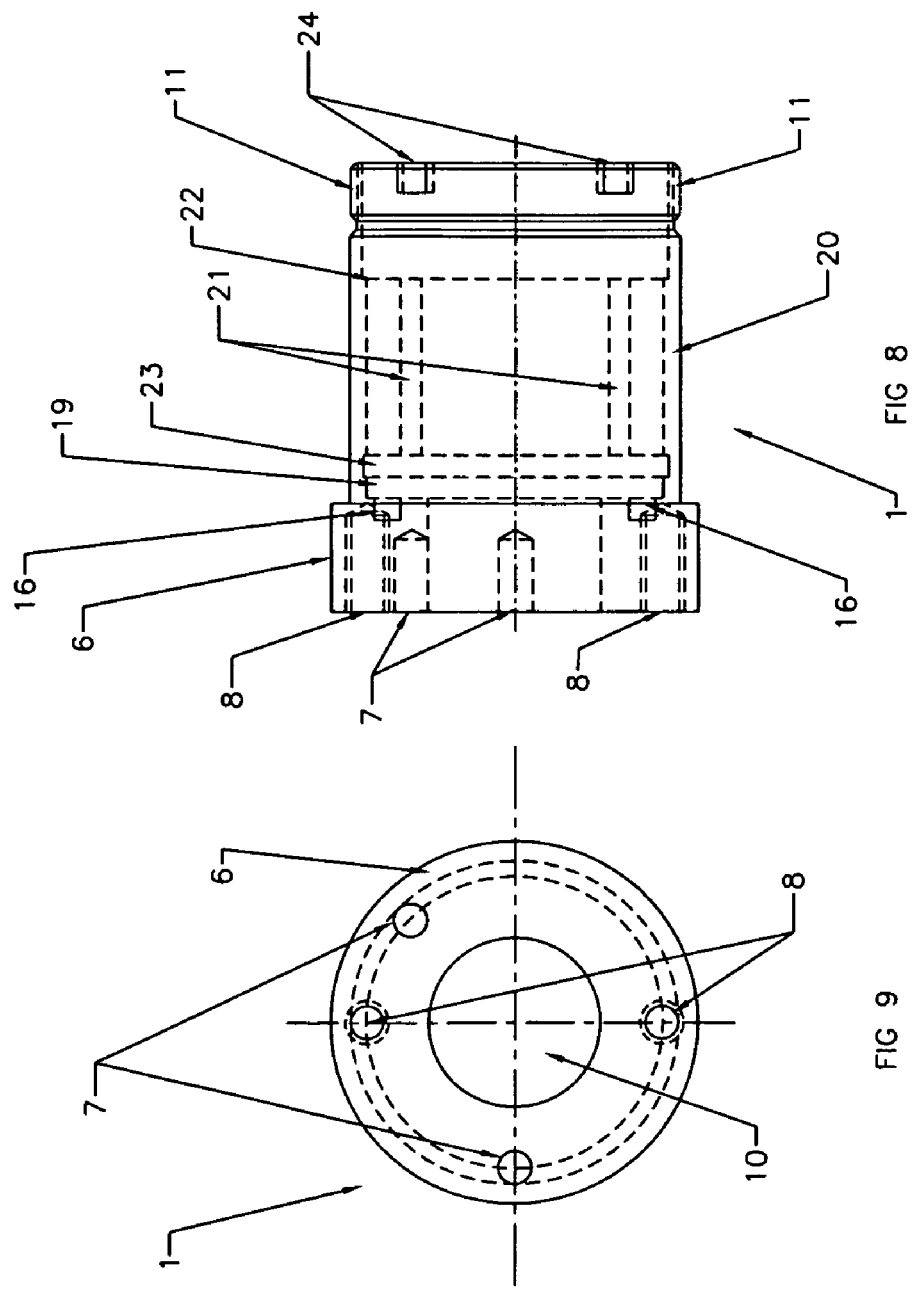

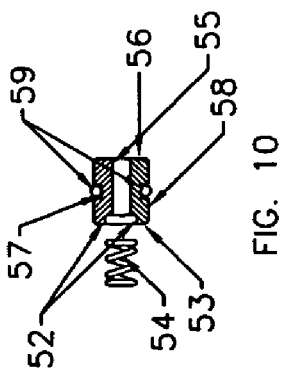
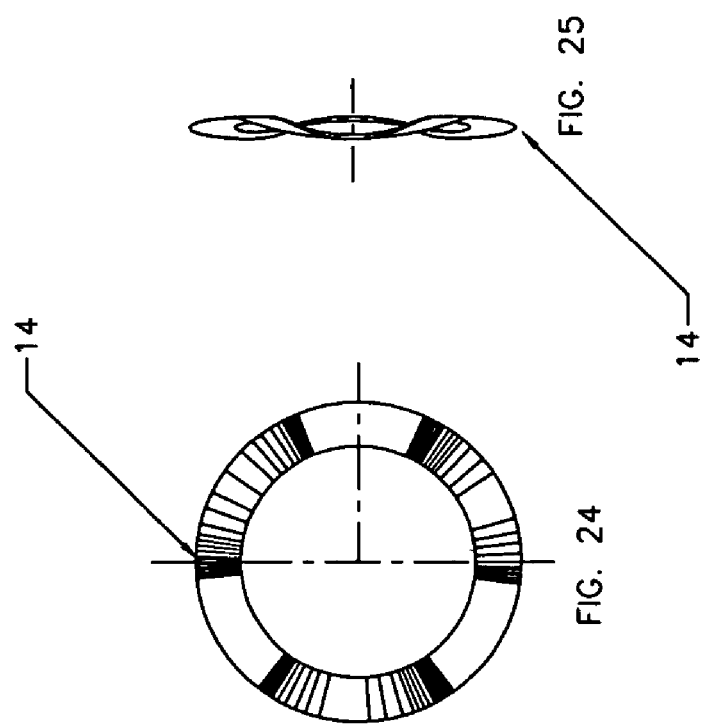

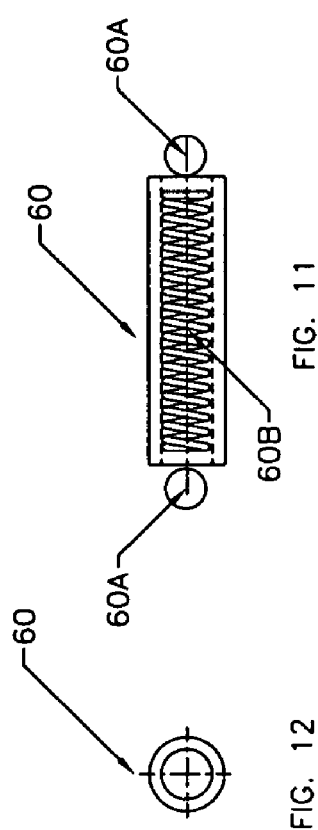

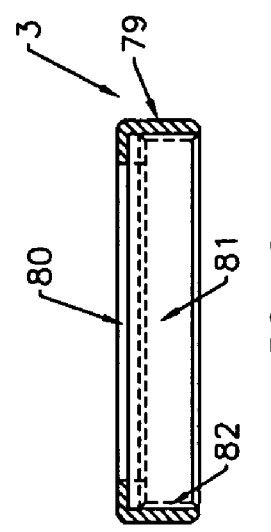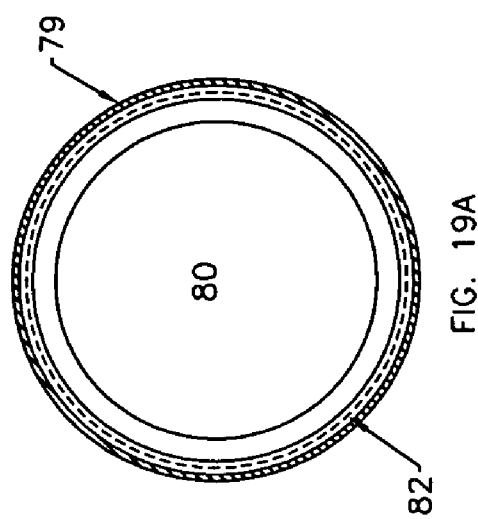

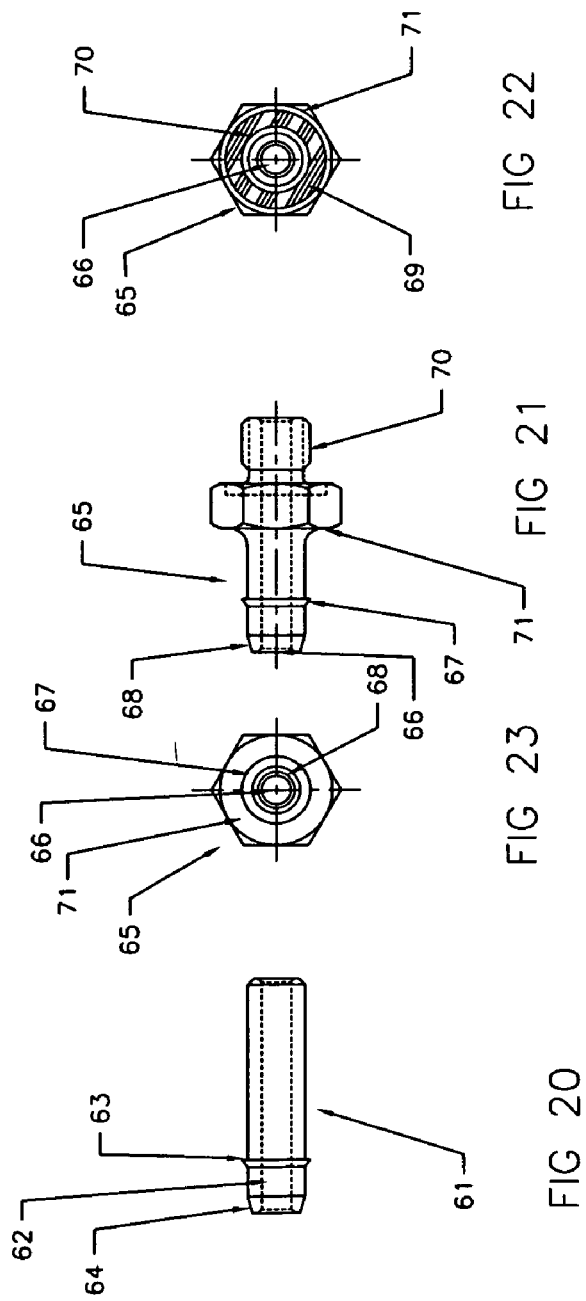

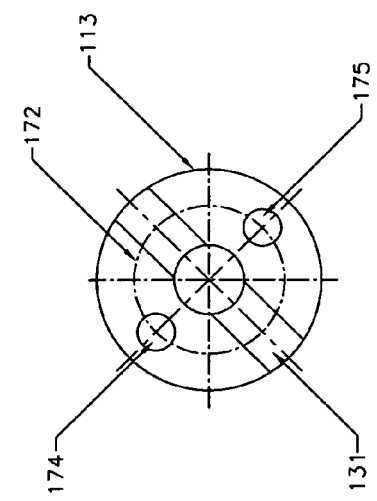
FIG. 38
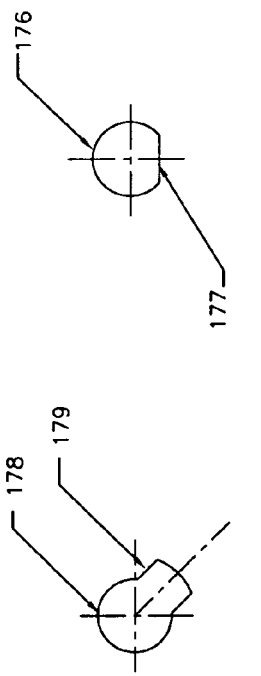
FIG. 29
FIG. 28
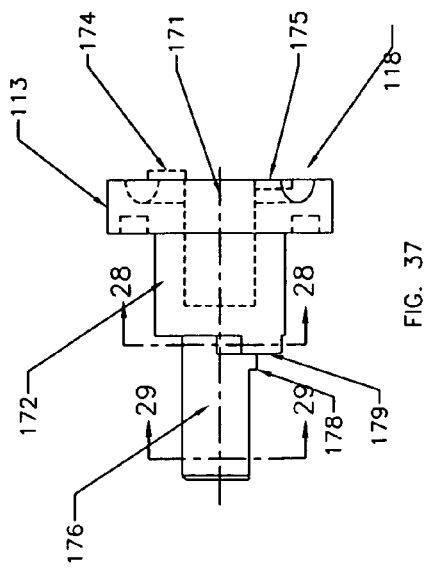
FIG. 37
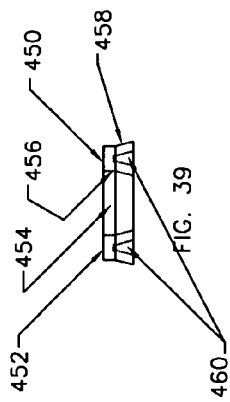
FIG. 39
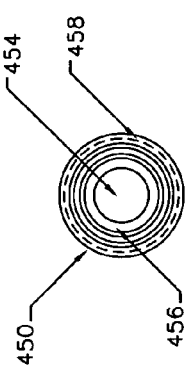
FIG. 40

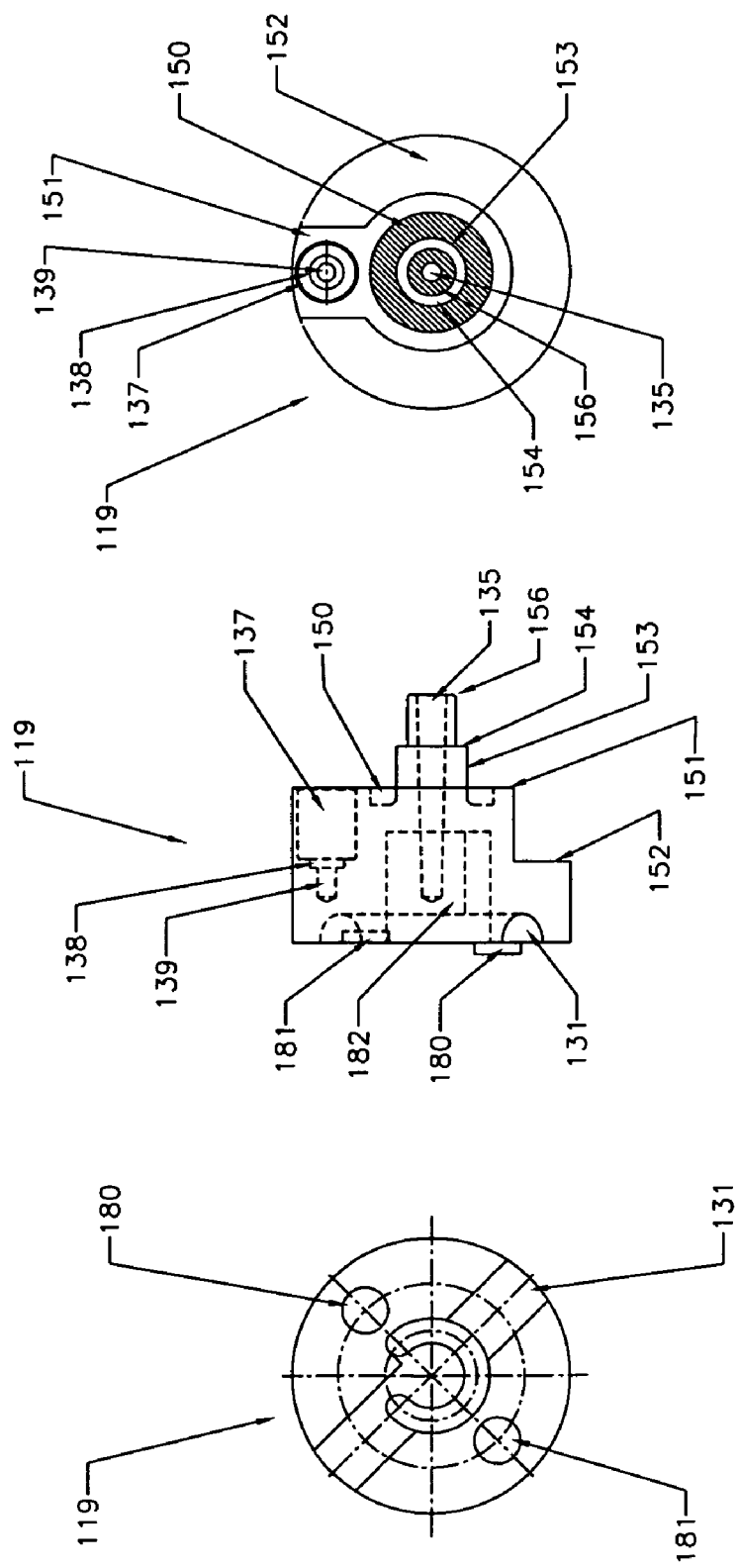

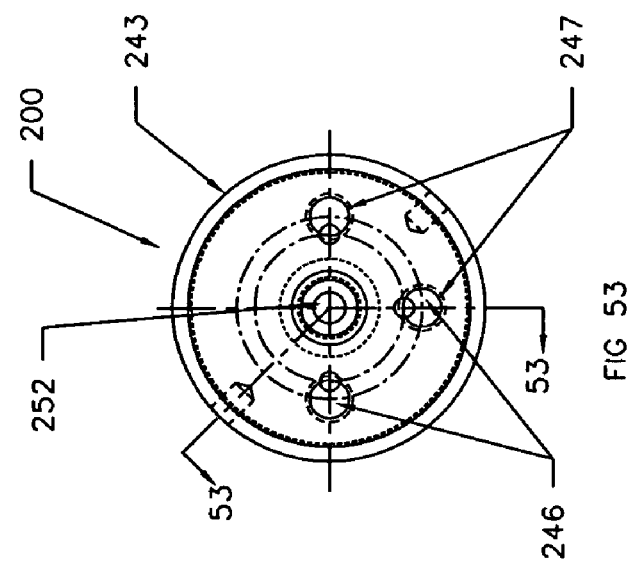
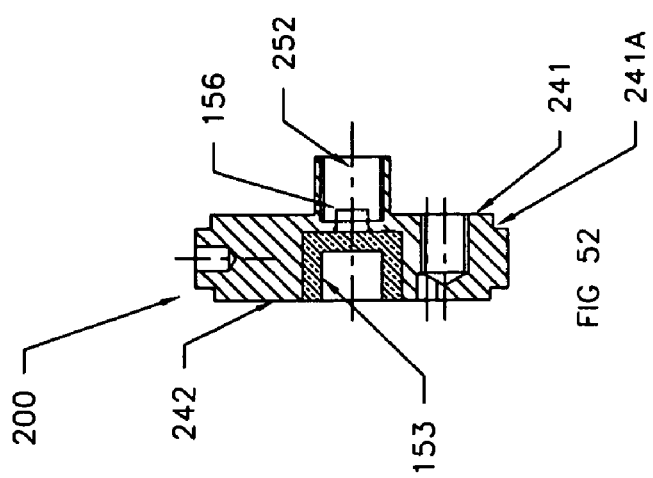

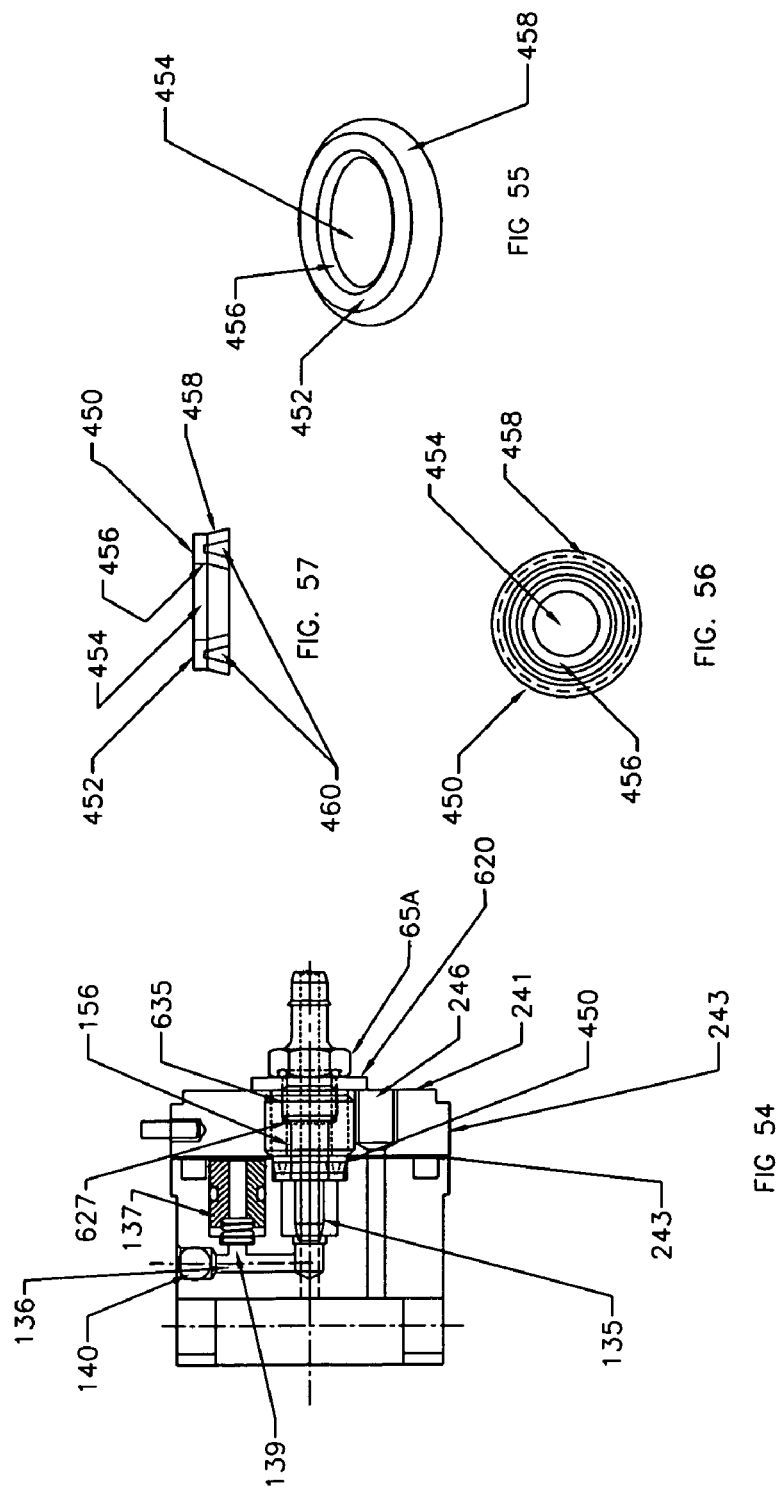

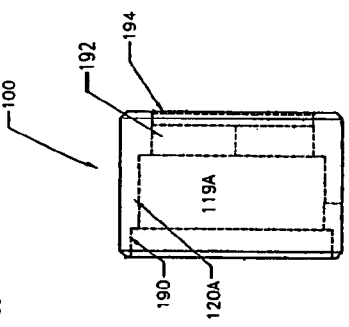
FIG 62
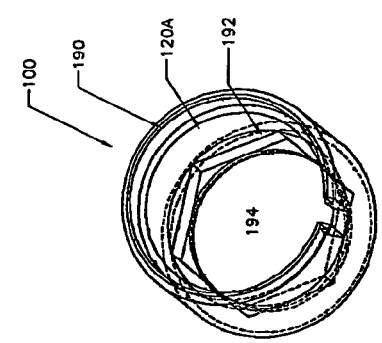
FIG 59
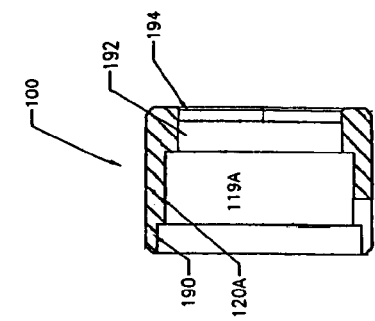
FIG 60
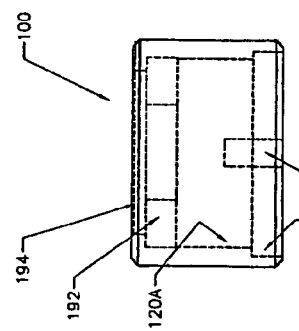
FIG 58
FIG 61

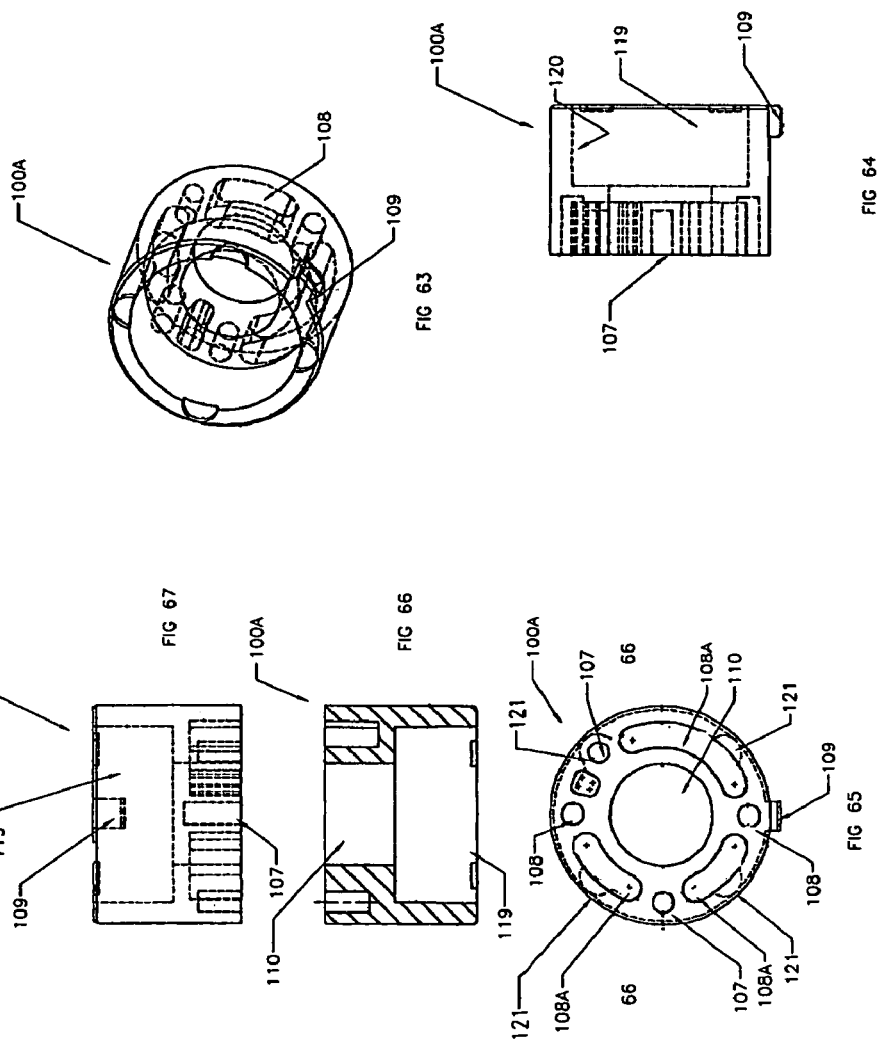

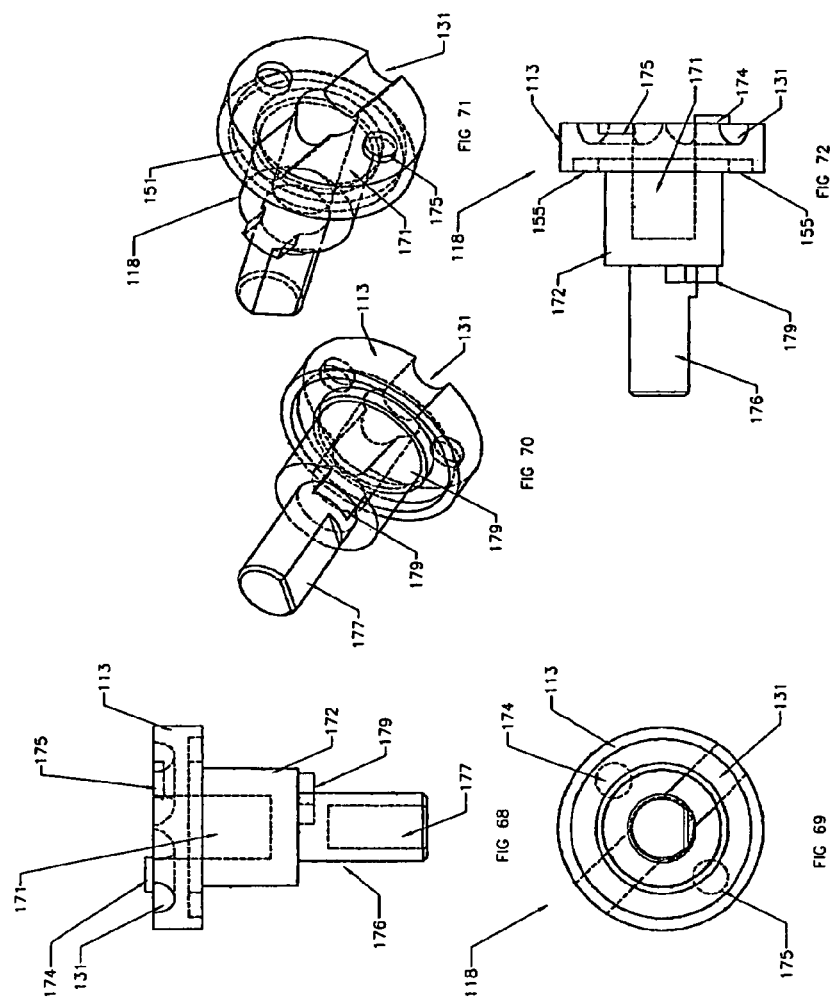

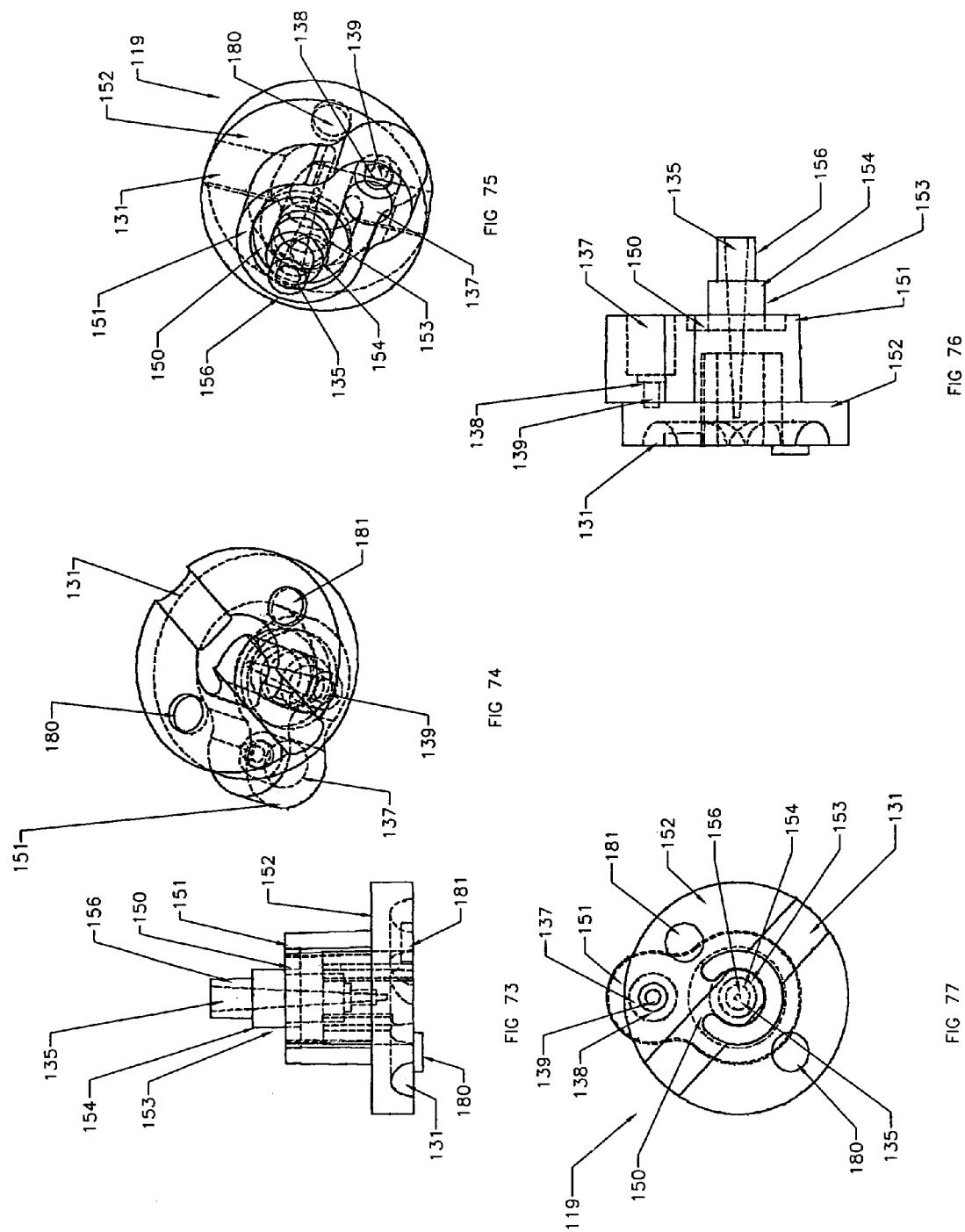

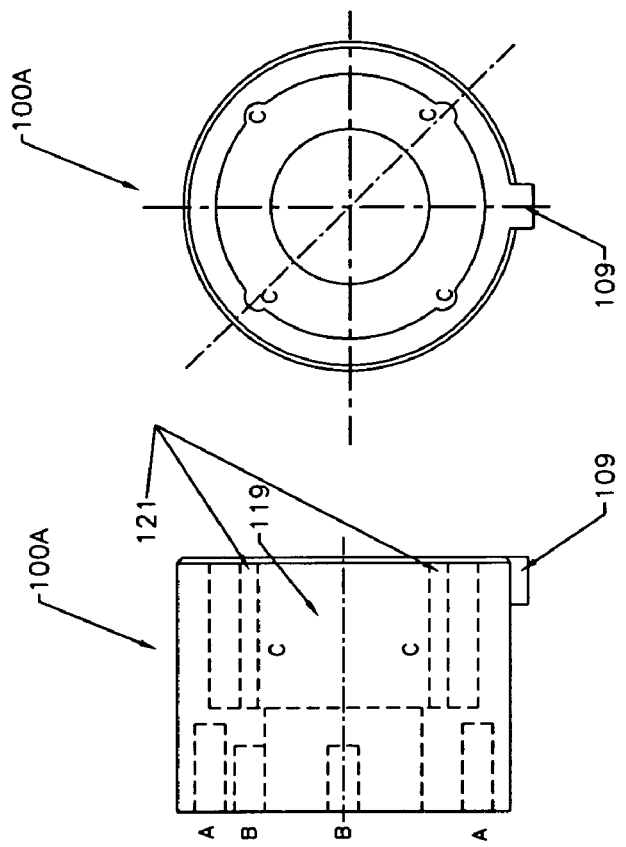
FIG. 84
FIG. 83
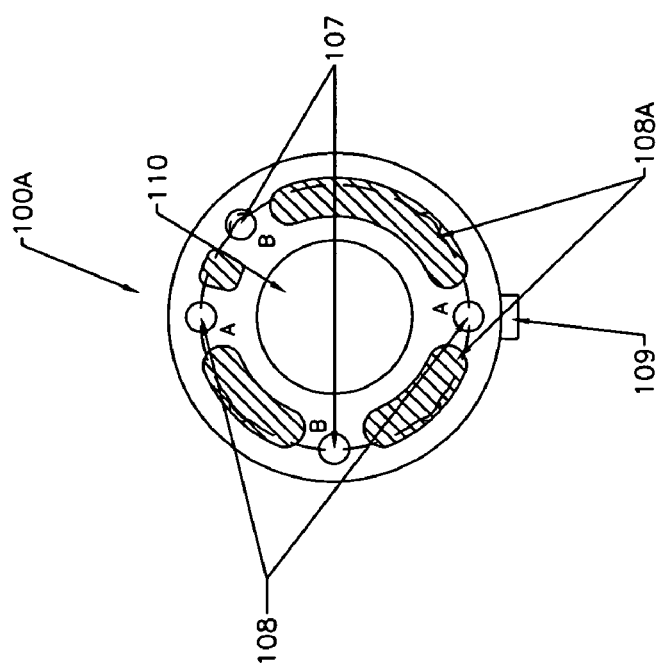
FIG. 82

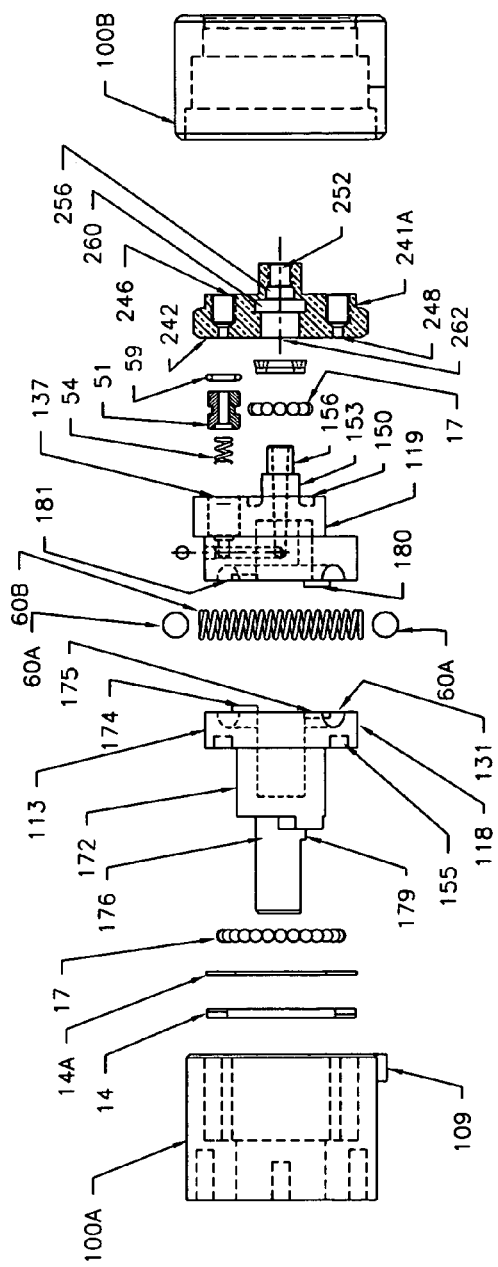
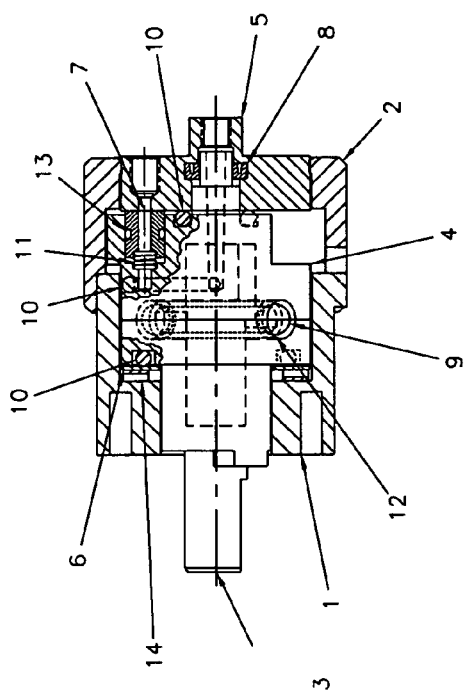

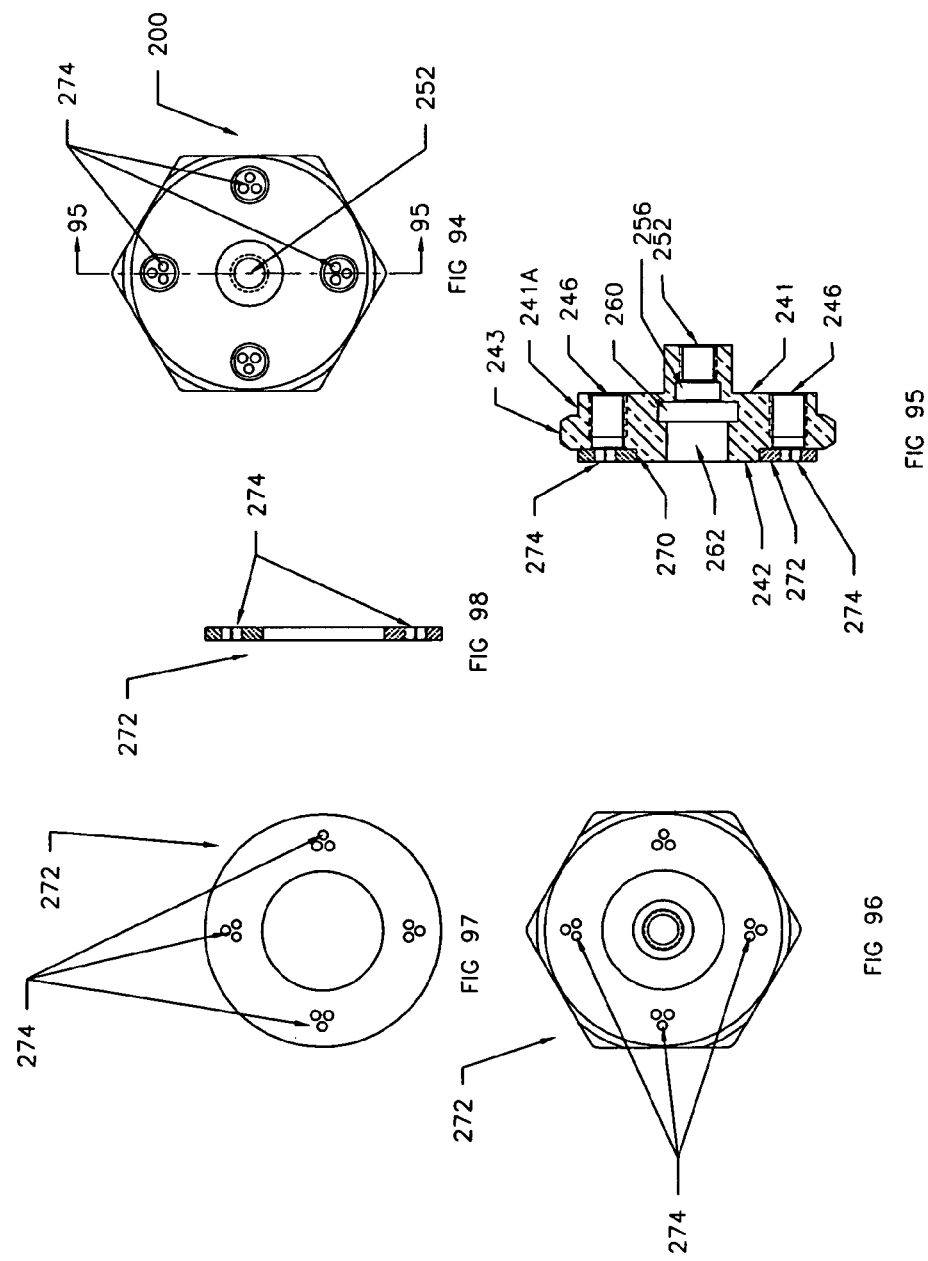

MULTI-PORT FLUID VALVE AND METHOD

CROSS-REFERENCE TO RELATED APPLICATION

This is a continuation application of U.S. Ser. No. 09/513,651 filed Feb. 25, 2000 now U.S. Pat. No. 6,725,881, the contents of which are incorporated herein by reference.

BACKGROUND OF THE INVENTION

1. Field of the Invention

This invention relates generally to valves. More particularly, the invention relates to valves having multiple ports.

2. Description of Related Art

Valve assemblies having multiple ports have existed for many years and have been used in a wide variety of applications. One such application is the use in dental medicine. A device known as a tooth de-scaler is used to remove plaque build-up on teeth. The device uses ultrasonic waves to effectuate the plaque removal.

While the device is being used, a stream of fluid is drawn into a small hose attached to the tip of the de-scaling device where the fluid exits. The fluid is used to wash away any loosened plaque. Such tooth de-scaling devices are designed to allow for three different fluid options. One option is regular tap water. A second option is bi-carbonate water. A third option is fluoride-fortified water.

Selection of the fluid source is accomplished by a multi-port valve which is required to handle pressures of approximately 65 psi which is a typical pressure at which tooth de-scaling devices are operated. The need to be able to shift quickly from one fluid option to another poses a number of problems.

One problem relates to the leakage of air from the multi-port valve. This is a problem that is common to most multi-valves. The key is to limit the leakage to less than one bubble per second to achieve what is known as "bubble tight" operation when the valve ports are plugged and the valve is submerged and pressurized. Some designs, for example, a conical valve and conical valve seat design does not sufficiently seal to minimize bubble production. As a result, an undesirable hissing sound emanates from such a valve assembly when exposed to fluid pressures in the 65 psi range.

It is therefore an object of the invention to provide a multi-port valve system that can minimize air leakage to no more than one bubble per second. Another object of the invention is to provide a valve having a "miniature envelope" which meets or exceeds the criteria to receive UL approval.

A still further object of the invention is to provide a bearing system that allows for effortless, maintenance-free rotation of the valve rotor within the valve housing.

SUMMARY OF THE INVENTION

The invention described herein employs a unique ball bearing support system for a multi-port valve assembly. The valve apparatus also employs slipper seals to provide a virtually air-tight seal between a rotor and stator of the assembly so that a multitude of fluids can be selectively transported through the valve in an efficient cost effective manner.

The rotor/stem assembly is supported by ball bearings situated in annular chases provided in the valve housing and in a top end of the rotor. Bores provided in the rotor receive the slipper seals which have through apertures to connect apertures in the rotor in fluid communication with apertures in the stator. Axial compression springs set within the rotor bores and within bores established in the slipper seals enhance the sealing effect by applying axial force to the slipper seals, forcing them into contact with the sealing face of the stator.

By rotating the rotor, a specific aperture in the stator is aligned with a fluid transmittal aperture/seal in the rotor. This aperture is in fluid communication with central fluid delivery apertures in the rotor and stator via a transverse channel. Alignment is accomplished by a system of detents and detent channels positioned to allow for alignment of the rotor apertures to the stator apertures. Stator apertures not aligned with the fluid receiving aperture are aligned with other apertures in the rotor to provide a means to rapidly depressurize lines that are either not in use or were in use just prior to the line presently selected. A vent bore situated in a side wall of the housing provides egress for any pressure buildup in unused lines.

The ball bearing support system coupled with the slipper seals provides a durable multi-port valve that can supply a selected fluid without compromising the integrity of the seals or ease with which the fluid lines can be selected for delivery of the desired fluid. These and other objects and features of the present invention will be apparent from a review of the drawings and a reading of the following detailed description of the invention.

BRIEF DESCRIPTION OF THE DRAWINGS

FIG. 1 is a plan view of a multi-port valve according to one embodiment of the invention.

FIG. 2 is a top view of a multi-port valve according to one embodiment of the invention.

FIG. 3 is a bottom view of a multi-port valve according to one embodiment of the invention.

FIG. 8 is a side perspective view of a valve housing according to one embodiment of the invention.

FIG. 9 is a bottom view of a valve housing according to one embodiment of the invention.

FIG. 10 is a side sectional view of a seal according to one embodiment of the invention.

FIG. 11 is a detent housing according to one embodiment of the invention.

FIG. 12 is an end view of a detent housing according to one embodiment of the invention.

FIG. 19 is a side sectional view of a bezel nut according to one embodiment of the invention.

FIG. 19a is a bottom view of a bezel nut according to one embodiment of the invention.

FIG. 20 is a side perspective view of a center barb according to one embodiment of the invention.

FIG. 21 is a side elevational view of a peripheral barb according to one embodiment of the invention.

FIG. 22 is a bottom view of a peripheral barb according to one embodiment of the invention.

FIG. 23 is a top view of a peripheral barb according to one embodiment of the invention.

FIG. 24 is a top view of a wave spring according to one embodiment of the invention.

FIG. 25 is a side view of a wave spring according to one embodiment of the invention.

FIG. 28 is a top sectional view of a portion of a valve assembly according to one embodiment of the invention.

FIG. 29 is a top sectional view of a portion of a valve assembly according to one embodiment of the invention.

FIG. 34 is a side view of a rotor/valve assembly bottom half according to one embodiment of the invention.

FIG. 35 is a top view of a rotor/valve assembly bottom half according to one embodiment of the invention.

FIG. 36 is a bottom view of a rotor/valve assembly top half according to one embodiment of the invention.

FIG. 37 is a side view of a rotor/valve assembly top half according to one embodiment of the invention.

FIG. 38 is a bottom view of a rotor/valve assembly top half according to one embodiment of the invention.

FIG. 39 is a sectional elevational view of a u-seal according to one embodiment of the invention.

FIG. 40 is a bottom view of a u-seal according to one embodiment of the invention.

FIG. 52 is a top view of a stator according to one embodiment of the invention.

FIG. 53 is a sectional view of a stator according to one embodiment of the invention.

FIG. 54 is a sectional view of a rotor/stator/barb/u-seal assembly according to one embodiment of the invention.

FIG. 55 is a perspective view of a u-seal according to one embodiment of the invention.

FIG. 56 is a bottom view of a u-seal according to one embodiment of the invention.

FIG. 57 is a sectional view of a u-seal according to one embodiment of the invention.

FIG. 58 is a side elevational view of a housing bottom half according to one embodiment of the invention.

FIG. 59 is a perspective view of a housing bottom half according to one embodiment of the invention.

FIG. 60 is a top view of a housing bottom half according to one embodiment of the invention.

FIG. 61 is a sectional view of a housing bottom half according to one embodiment of the invention.

FIG. 62 is a side view of a housing bottom half according to one embodiment of the invention.

FIG. 63 is a perspective view of a housing top half according to one embodiment of the invention.

FIG. 64 is a side view of a housing top half according to one embodiment of the invention.

FIG. 65 is a top view of a housing top half according to one embodiment of the invention.

FIG. 66 is a sectional view of a housing top half according to one embodiment of the invention.

FIG. 67 is a side elevational view of a housing top half according to one embodiment of the invention.

FIG. 68 is a side view of a valve stem portion of a valve stem/rotor assembly according to one embodiment of the invention.

FIG. 69 is a top view of a valve stem portion of a valve stem/rotor assembly according to one embodiment of the invention.

FIG. 70 is a perspective view of a valve stem of a valve stem/rotor assembly according to one embodiment of the invention.

FIG. 71 is another perspective view of a valve stem/rotor assembly according to one embodiment of the invention.

FIG. 72 is a side view of a valve stem of a valve stem/rotor assembly according to one embodiment of the invention.

FIG. 73 is a side view of a rotor of a valve stem/rotor assembly according to one embodiment of the invention.

FIG. 74 is a perspective view of a rotor of a valve stem/rotor assembly according to one embodiment of the invention.

FIG. 75 is another perspective view of a rotor of a valve stem/rotor assembly according to one embodiment of the invention.

FIG. 76 is a side view of a rotor of a valve stem/rotor assembly according to one embodiment of the invention.

FIG. 77 is a top view of a rotor of a valve stem/rotor assembly according to one embodiment of the invention.

FIG. 82 is a bottom view of a top portion of a housing according to one embodiment of the invention.

FIG. 83 is a side view of a top portion of a housing according to one embodiment of the invention.

FIG. 84 is a top view of a top portion of a housing according to one embodiment of the invention.

FIG. 87 is an exploded view of a multiport fluid valve according to one embodiment of the invention.

FIG. 87a is a side elevational view of an assembled multiport fluid valve according to one embodiment of the invention.

FIG. 94 is a top view of a stator according to one embodiment of the invention.

FIG. 95 is a sectional view of a stator according to one embodiment of the invention.

FIG. 96 is a bottom view of a stator according to one embodiment of the invention.

FIG. 97 is a bottom view of a seal face according to one embodiment of the invention.

FIG. 98 is a side view of a seal face according to one embodiment of the invention.

DETAILED DESCRIPTION OF THE PREFERRED EMBODIMENTS

Figure 4:
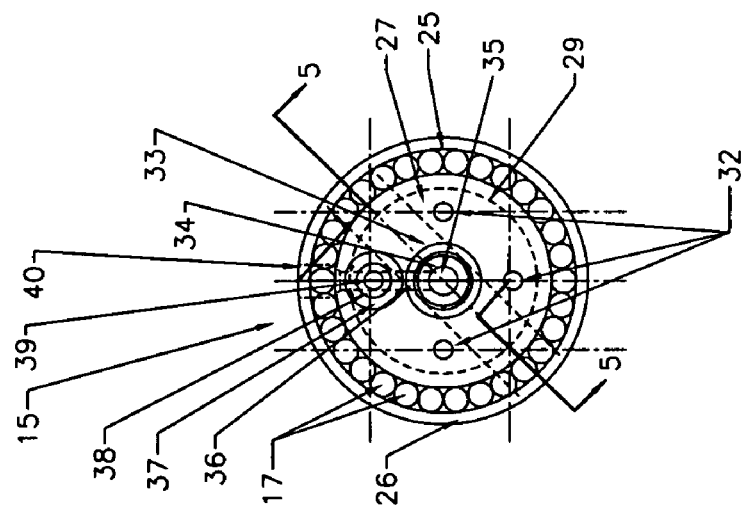
FIG. 4 is a top view of a rotor according to one embodiment of the invention.

Referring to FIG. 1, a multi-port valve according to one embodiment of the invention is shown. The valve comprises a housing 1, a valve stator 2 that is sized to fit within housing 1, a bezel nut 3 that has threading (as shown in FIG. 19), situated about an inner annular wall of bezel nut 3, a valve stem 4 that engages a rotor (shown in FIGS. 4 and 5), situated within housing 1, a center barb 5 affixed to stator 2 via mated threading or permanent affixation, that provides a common channel for fluids transported through the valve, and peripheral barbs (not shown) that provide fluid selectable channels for fluid transported through lines (not shown) that are releasably secured to the peripheral barbs.

Housing 1 has a radially extended base 6 to accommodate attachment bores. As shown in FIGS. 3 and 9, optional pin locator bores 7 can be provided to engage locator pins (not shown) projecting from a larger assembly to which the multi-port valve body is attached. Optional bore holes 8 can also be provided to accept mechanical fasteners (not shown). If threaded mechanical fasteners are used, bore holes 8 can be provided with threading 9 extending axially along the portions of housing 1 that define bore holes 8.

Radially extended base 6 has portions that define a large bore 10 through which a portion of valve stem 4 exits. At a top end of housing 1, external threading 11 is provided to matingly engage threading 82 of bezel nut 3.

Housing 1 has further portions which define a vent bore 12 that allows for depressurization of peripheral channels not connected to the central channel. Situated in planes within the circumference of vent bore 12 are a valve stem top annular plate 13, a wave spring 14 (shown in FIGS. 24 and 25), an optional washer 14a (shown in FIG. 87), and a bottom edge of rotor 15.

Figure 8A:
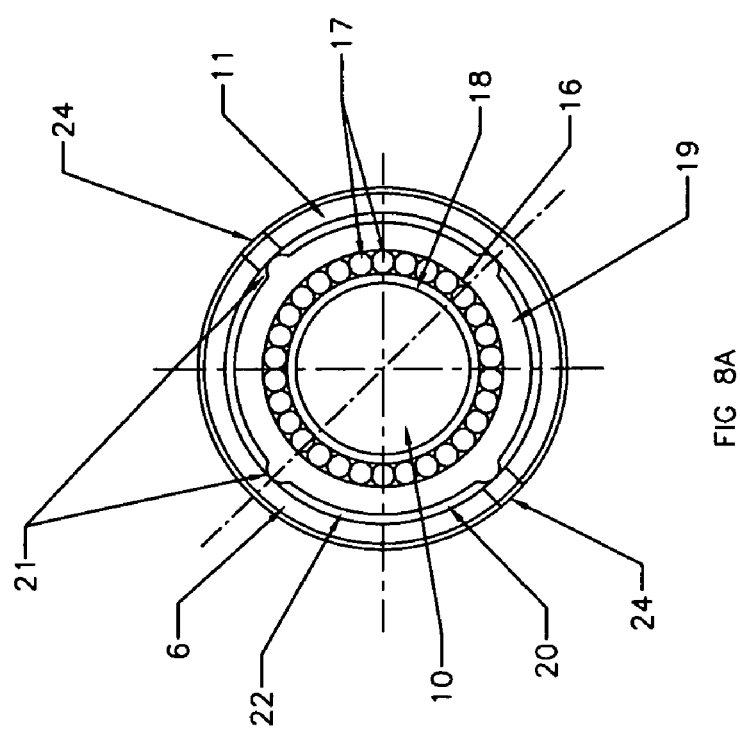
FIG. 8a is a top view of a valve housing according to one embodiment of the invention.
Figure 18:
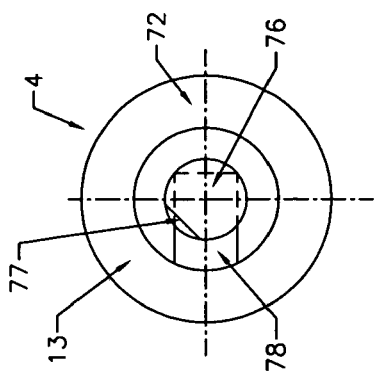
FIG. 18 is a bottom view of a valve stem according to one embodiment of the invention.
Figure 15:
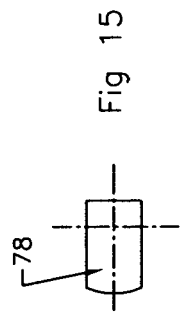
FIG. 15 is a sectional view of a key portion of a valve stem according to one embodiment of the invention.
Figure 13:
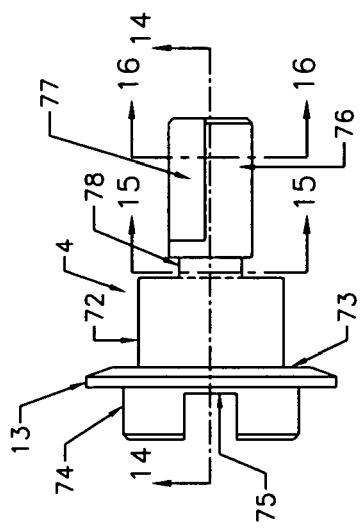
FIG. 13 is a side elevational view of a valve stem according to one embodiment of the invention.
Figure 17:
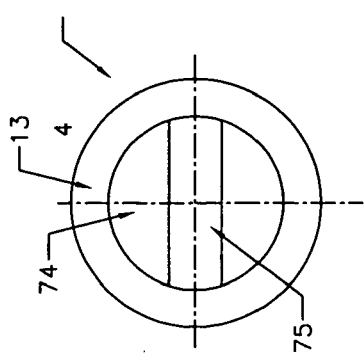
FIG. 17 is a top view of a valve stem according to one embodiment of the invention.
Figure 14:
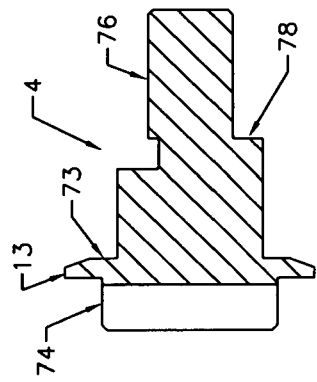
FIG. 14 is a side sectional view of a valve stem according to one embodiment of the invention.
Figure 16:
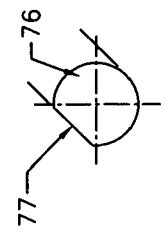
FIG. 16 is a sectional view of a chamfered distal end of a valve stem according to one embodiment of the invention.

Referring to FIGS. 8 and 8a, housing 1 has portions which define an annular housing chase 16 for containing ball bearings that support the valve stem 4 and a rotor (not shown), features which are described in more detail below. Extending axially upwardly from radially extended base 6 is annular wall 18 which defines aperture 10 and forms an inner annular wall of annular housing chase 16. Extending radially from a top edge of an outer annular wall of annular housing chase 16 is an annular chamfer 19 which has the function of facilitating loading of ball bearings 17 into annular housing chase 16.

Ball bearing 17 loading is accomplished efficiently by placing a plug (not shown), in aperture 10 and pouring ball bearings 17 into housing 1. Annular chamfer 19 cause ball bearings 17 to flow into annular housing chase 16. This process is continued until annular housing chase 16 has a supply of ball bearings 17 adequate to support valve stem 4 and the aforesaid rotor. In a preferred embodiment, annular housing chase 16 is not filled to maximum capacity to allow free movement of the ball bearings and thus, free movement of valve stem 4 and rotor 15.

Ball bearings 17 may be made of steel or any engineering grade of plastic or polymer. In a preferred embodiment, ball bearings 17 are made from Delrin® (Dupont), an acetyl-based resin.

Situated in a main annular wall 20 of housing 1 are a plurality of detent channels 21 which releasably arrest movement of rotor 15 within housing 1. The number and placement of detent channels 21 determine the number of positions and angular displacement of rotor 15 relative to stator 2.

To accommodate the dimensions of stator 2, main annular wall 20 is bored such that an annular shoulder 22 is formed at a top end of main annular wall 20. Annular shoulder 22 defines a top end of detent channels 21. Alternatively, stator 2 can be downsized to fit within the dimensions of main wall 20 without further boring. The thickness of wall 20 can vary and is only limited in terms of minimal thickness to a thickness that will maintain the integrity of housing 1 after detent channels 21 are formed by boring or broaching.

If broaching is the procedure used to form detent channels 21, relief channel 23 is formed to allow an avenue of release for the cutter used in the broaching process. If a boring process is used, formation of relief channel 23 can be eliminated.

To fix rotational and axial movement of stator 2 within housing 1, at least one slot 24 is formed in a top edge of housing 1 to receive pins 45 extending from a radial edge of stator 2. Preferably at least two slots 24 are provided to stabilize stator 2 within housing 1.

Figure 32:
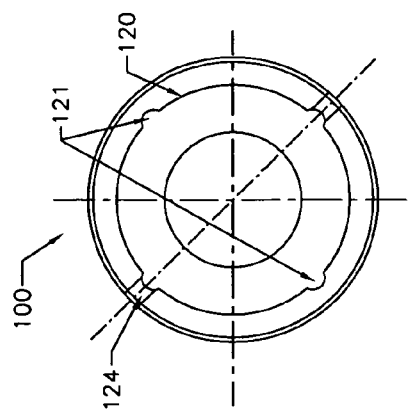
FIG. 32 is a top view of a housing according to one embodiment of the invention.
Figure 31:
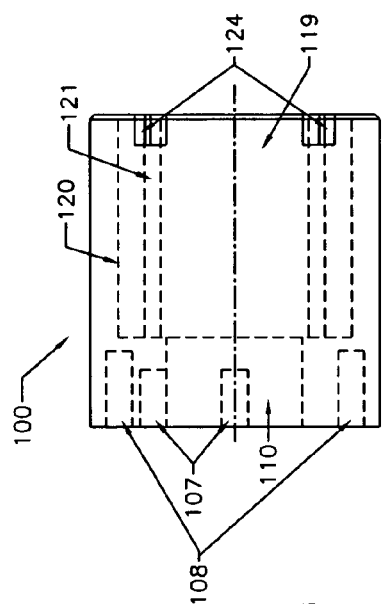
FIG. 31 is a side view of a housing according to one embodiment of the invention.
Figure 33:
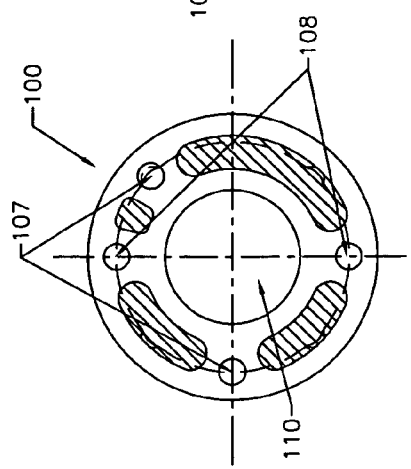
FIG. 33 is a bottom view of a housing according to one embodiment of the invention.
Figure 43:
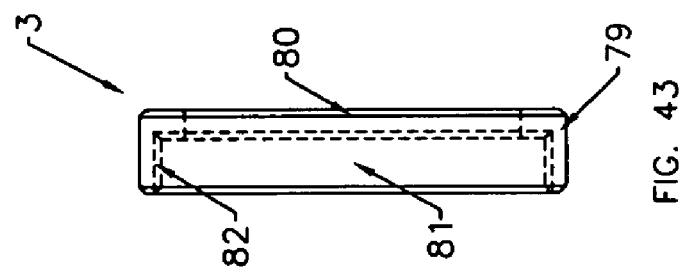
FIG. 43 is a side view of a bezel nut according to one embodiment of the invention.
Figure 42:
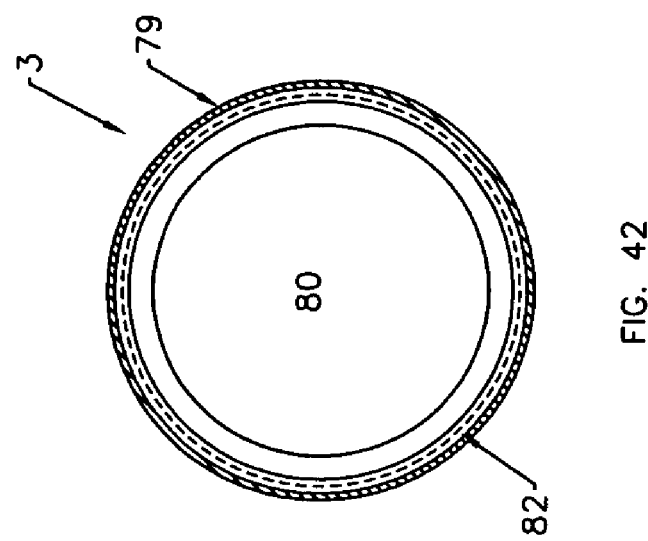
FIG. 42 is a bottom view of a bezel nut according to one embodiment of the invention.

FIGS. 31–33 show a molded version of housing 1, designated housing 100 having optional pin locator bores 107 in a top surface that can be provided to engage locator pins (not shown) projecting from a larger assembly to which the multi-port valve body is attached. Optional bore holes 108 can also be provided to accept mechanical fasteners (not shown). If threaded mechanical fasteners are used, bore holes 108 can be provided with threading extending axially along the portions of housing 100 that define bore holes 108.

Situated in a main annular wall 120 of housing 100 are a plurality of detent channels 121 which releasably arrest movement of rotor/valve stem assembly 115 within housing 100. The number and placement of detent channels 121 determine the number of positions and angular displacement of rotor/valve stem assembly 115 relative to stator 200. Molded slots 108*a* are provided to allow for uniform cooling of the material used to mold housing 100.

To fix rotational and axial movement of stator 2 relative to housing 100 if stator 2 is combined with housing 100, at least one slot 124 is formed in a top edge of housing 1 to receive pins 45 extending from a radial edge of stator 2. Preferably at least two slots 124 are provided to stabilize stator 2 within housing 100.

A main housing bore 119 is formed in housing 100 to receive in rotational engagement, rotor/valve stem assembly 115. Formed on a top surface of housing 100 is aperture 110 that is sized to receive the main valve stem body 172 portion of rotor/valve stem assembly 115 that project out of housing 100.

Figure 5:
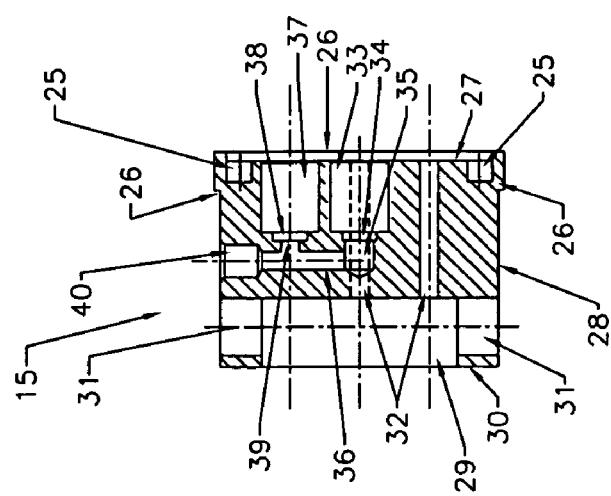
FIG. 5 is a sectional side view of a rotor according to one embodiment of the invention.

Referring now to FIGS. 4 and 5, rotor 15 is shown which is sized to fit within housing 1 so that it can freely rotate within housing 1. Rotation of rotor 15 allows for the selection of ports contained within stator 2 to be engaged for delivery of fluids. Rotor 15 has portions which define an annular rotor chase 25 for receiving ball bearings 17 which support stator 2. An annular top exterior rotor wall 26 extends axially upwardly from top face 27 of rotor 15. Top exterior wall 26 defines an outer wall of annular rotor chase 25 and functions to align stator 2 with rotor 15 by mating with a portion of stator 2 that is sized to fit within the inner diameter of top exterior wall 26.

In one embodiment, top exterior wall 26 extends radially from side wall 28 of rotor 15 to provide sufficient thickness to maintain the integrity of the wall 26 to perform the alignment function. In alternate embodiments, extension of top exterior wall 26 radially outwardly from side wall 28 can be eliminated by downsizing the overall diameter of stator 2 to fit within a smaller inner diameter of top exterior wall 26 or by increasing the thickness of side wall 28 to match the outside diameter of exterior wall 26.

Rotor 15 has portions which define a main rotor aperture 29 which is sized to receive a portion of valve stem 4. Aperture 29 opens on a bottom face 30 of rotor 15. Rotor 15 has further portions which define detent housing apertures 31 which are situated in opposite ends of side wall 28 and which open into main rotor aperture 29. Detent housing apertures 31 are sized to receive detent housing 60 as shown in FIGS. 11 and 12.

In a preferred embodiment, detent housing 60 is a hollow cylindrical tube. Preferably detents 60*a* (such as ball bearings shown in FIG. 11), and a detent spring 60*b* are placed within detent housing 60. Detents 60*a* are free within detent housing 60 or are retained via crimping or adhesives. Detents 60*a* are maintained at the ends of detent housing 60 by detent spring 60*b* situated within detent housing 60 between detents 60*a*. The detents 60*a* are sized to releasably lock within detent channels 21.

Rotor 15 has yet further portions which define a plurality of axial apertures 32 which run from top face 27 to main rotor aperture 29. The number of axial apertures 32 is invariable and can be limited to one. All apertures 32 are in fluid communication with vent bore 12 which allows for the depressurization of any channels that are not in use or have been previously used. Venting can also be accomplished by utilizing a clearance around rotor 15 and housing 1 along with a clearance between rotor 15 and stator 2.

Situated in the approximate center of top face 27 is a main fluid delivery bore 33. Main fluid delivery bore 33 is not in fluid communication with main aperture 29. Extending downwardly and concentrically with main fluid bore 33 is fluid delivery counterbore 34 which is sized to receive and engage a slipper seal as more fully described below. Extending downwardly and concentrically with fluid delivery counterbore 34 is fluid delivery aperture 35 which connects fluid delivery bore 33 with a transverse fluid channel 36.

Extending downwardly from top face 27 and radially outwardly from fluid delivery bore 33 is fluid conveying bore 37 which does not extend axially to main aperture 29. Extending downwardly and concentrically within the diameter of fluid conveying bore 37 is fluid conveying counterbore 38 which is sized to receive and engage a fluid receiving slipper seal as more fully described below.

Extending downwardly and concentrically within the diameter of fluid conveying counterbore 38 is fluid conveying aperture 39 which connects fluid conveying bore 37 with transverse fluid channel 36. Fluid delivery bore 33 and fluid conveying bore 37 are in fluid communication via transverse fluid channel 36.

In one embodiment, transverse fluid channel 36 is formed by boring through side wall 28 at a position selected so that the walls of transverse fluid channel 36 intersect the fluid delivery and conveying apertures 35 and 39, respectively. To seal off transverse fluid channel 36, a counterbore 40 is provided that is concentric with channel 36. Counterbore 40 is sized to receive a plug that can be made from any suitable material such as rubber or steel and can be shaped in the form of ball bearing 17.

Figure 6:
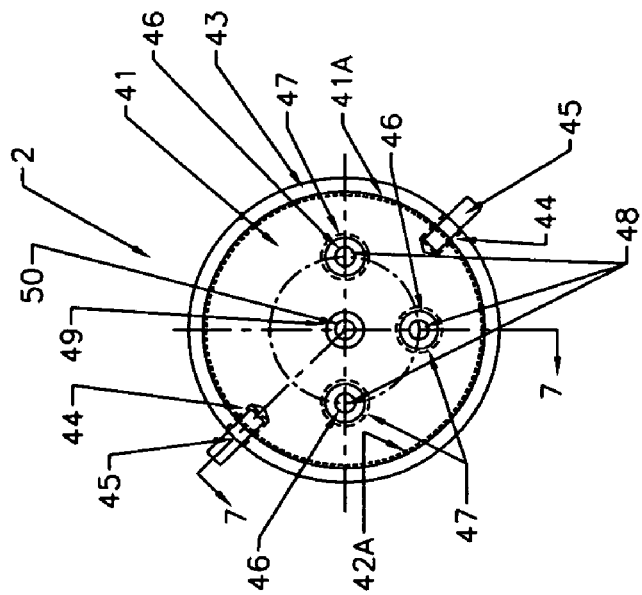
FIG. 6 is a top view of a stator according to one embodiment of the invention.
Figure 7:
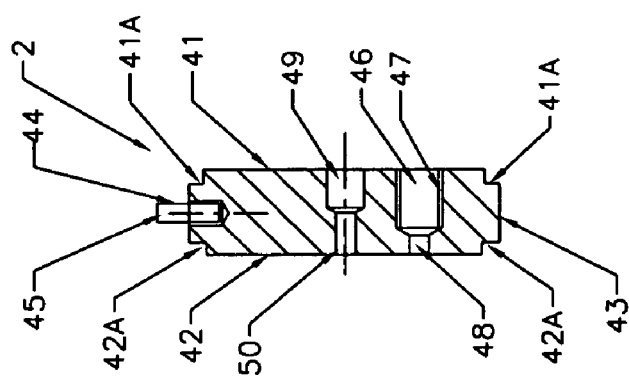
FIG. 7 is a sectional side view of a stator according to one embodiment of the invention.

Referring now to FIGS. 6 and 7, stator 2 is shown which has, in a preferred embodiment, a central aperture and a plurality of peripheral apertures to allow for the selective delivery of fluids via fluid communication with rotor 15. Stator 2 has a stator top face 41 a stator bottom face 42, both of which, in a preferred embodiment, are annular in shape and have diameters that are less than the diameter of a stator side wall 43 which, in a preferred embodiment has a diameter equal to the outer diameter of top exterior wall 26 of housing 1. The junction of stator bottom face 42 and stator side wall 43 form bottom shoulder 42*a* which centers stator 2 within top exterior wall 26. Stator bottom face 42 is sized to fit within the inner diameter of top exterior wall 26.

The junction of stator top face 41 and stator side wall 43 form top shoulder 41*a* which centers stator 2 within an aperture provided in bezel nut 3. Stator top face 41 is sized to fit within the diameter of bezel nut aperture 80.

Provided in opposite ends of stator side wall 43 are pin bores 44 which are sized to receive pins 45. Pins 45 when affixed to stator 2 extend radially from stator side wall 43. Pins 45 are sized to fit within the dimensions of slots 24 of housing 1. The combination of top exterior wall 26, bottom shoulder 42*a*, top shoulder 41*a*, bezel nut aperture 80, slots 24 and pins 45 secure the location of stator 2 relative to housing 1 and rotor 15 along the x, y and z axes.

Extending downwardly from stator top face 41 to a point short of stator bottom face 42 are a plurality of stator bores 46 which align with the axial apertures 32 and fluid conveying bore 37 of rotor 15 when stator 2 is placed on rotor 15. In a preferred embodiment, stator bores 46 having threading 47 to receive threaded barbs 65. In an alternate embodiment, barbs can be permanently fixed to stator bores 46 via methods such as brazing.

As shown in FIGS. 21–23, threaded barbs 65 have portions which define a threaded barb aperture 66. To receive a hose (not shown), for fluid transmission, threaded barbs 65 have an annular flange 67 that prevents retraction of the fluid conveying hose. To ease assembly of the hose to threaded barb 65, a top end 68 of threaded barb 65 is chamfered.

Figure 44:
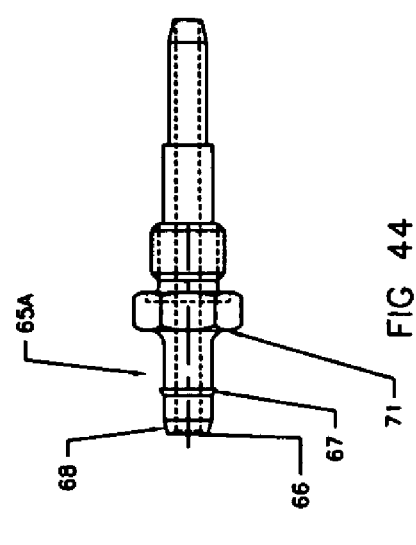
FIG. 44 is a side view of a center barb according to one embodiment of the invention.
Figure 45:
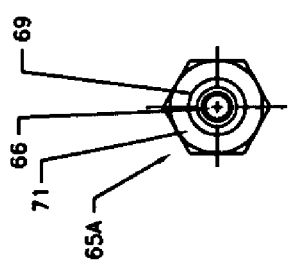
FIG. 45 is a top view of a center barb according to one embodiment of the invention.
Figure 46:
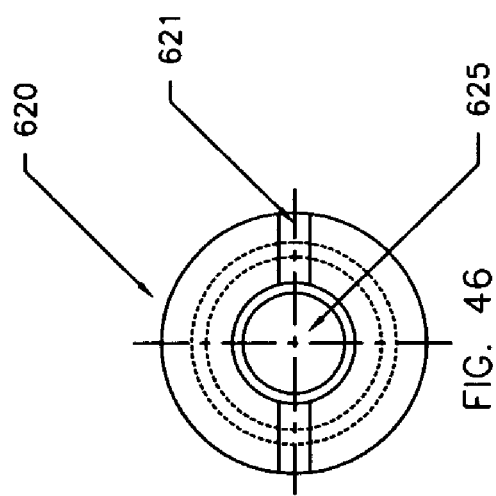
FIG. 46 is a top view of gland nut according to one embodiment of the invention.
Figure 47:
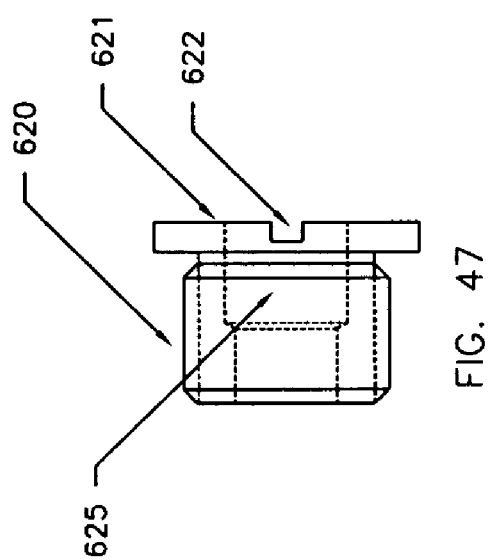
FIG. 47 is a side view of a gland nut according to one embodiment of the invention.

To ensure an airtight seal, threaded barb 61 has an annular threaded barb channel 69 into which an o-ring (not shown), is placed. When threaded barb male threads 70 are mated to female threads 47 situated in stator 2 by torquing threaded barb 61 into stator bore 46, treaded barb 61 is torqued sufficiently tight to compress the o-ring to ensure an air-tight seal. Of course, the male to female threading can be reversed with respect to barb 69 and stator 2. To aid torquing threaded barb 61, a radially extended portion 71 of a treaded barb side wall 72 is provided. Radially extended portion 71 is shown as having an octagon-shaped perimeter. The perimeter shape of radially extended portion 71 can have any regular or irregular geometric shape. An alternate embodiment of threaded barb 65 in a non-threaded version 65a for connection via brazing is shown in FIGS. 44 and 45.

Referring again to FIGS. 6 and 7, extending downwardly and concentrically from stator bores 46 are fluid apertures 48 which are in fluid communication with axial apertures 32 and fluid conveying bore 37 via slipper seals 51. The number of peripheral stator bores 46 and fluid apertures 48 establishes the number of possible fluid selections that can be made. The number of peripheral stator bores 46 is invariable and can be limited to one. Preferably, one to eight peripheral stator bores 46 are provided.

Extending downwardly from stator top face 41 to a point short of stator bottom face 42 and situated in the approximate center of stator top face 41 is stator fluid delivery bore 49. Extending downwardly and concentrically with stator fluid delivery bore 49 is stator fluid delivery aperture 50 which is in fluid communication with fluid delivery bore 33 of rotor 15 via slipper seal 51. In a preferred embodiment, fluid delivery barb 61 (as shown in FIG. 20), is permanently fixed to stator fluid delivery bore 49 via brazing or other suitable method of affixation. In an alternate embodiment, stator fluid delivery bore 49 can be provided with threading to receive a barb that has mated threading like threaded barb 65 shown in FIGS. 21–23.

In a preferred embodiment, as shown in FIG. 20, fluid delivery barb 61 has portions which define barb aperture 62. To secure a hose (not shown), delivery barb 61 has an annular flange 63. To ease assembly of an appropriately sized hose to delivery barb 61, a top end 64 of delivery barb 61 is chamfered.

Referring now to FIG. 10, a slipper seal 51 is shown which functions as a bridge between rotor 15 and stator 2 to link, in fluid communication, the apertures and bores of rotor 15 with the apertures and bores of stator 2. Slipper seal 51 is preferably cylindrical in shape with a slipper bore 52 extending downwardly from a slipper seal top face 53 sized to receive an axial compression spring 54. Extending downwardly from and concentrically with slipper bore 52 is through aperture 55 which exits on a slipper seal bottom face 56. An annular o-ring groove 57 is provided in a slipper side wall 58 for receiving an o-ring 59.

Figure 89:
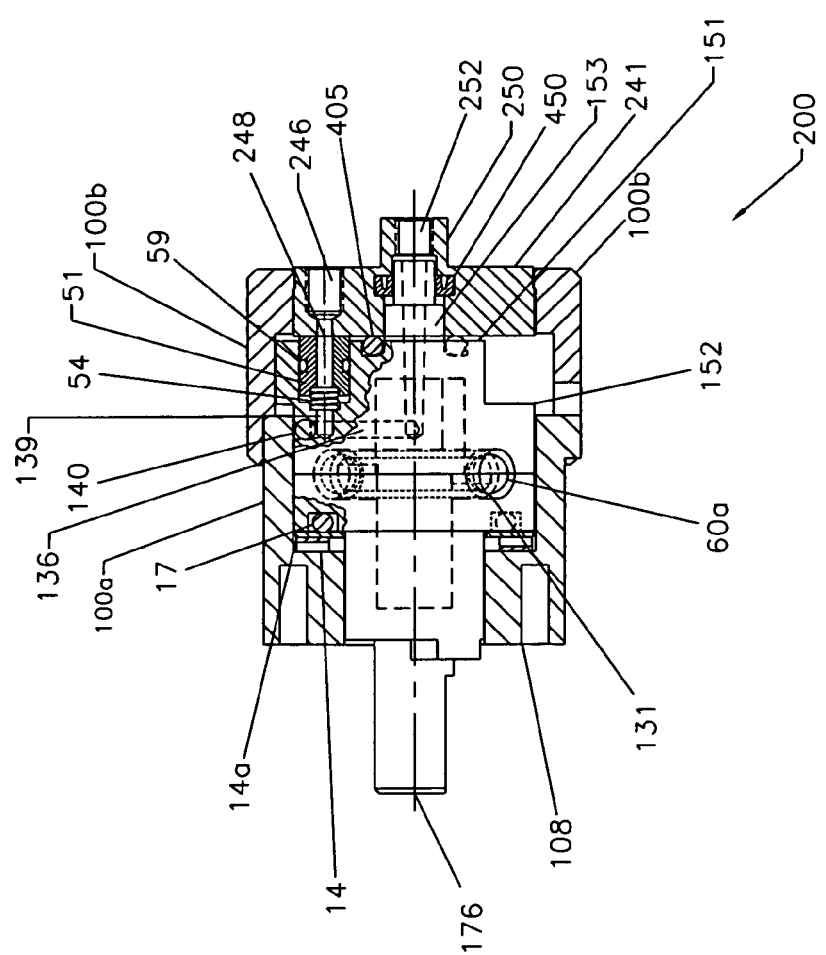
FIG. 89 is a side elevational view of a multiport fluid valve according to one embodiment of the invention.

Slipper seal 51 is sized to fit within fluid conveying bore 33 and fluid conveying bore 37. Axial compression spring 54 is sized to fit within fluid delivery counterbore 34 and fluid receiving bore 37 of rotor 15. O-ring 59 has an outside diameter that is sufficiently large to create a fluid seal between rotor 15 and slipper seal 51. FIG. 89 shows a slipper seal embodiment used in conjunction with a rotor/valve stem assembly 115 described in detail below.

Slipper seal 51 can be made from a variety of materials that have the ability to conform to bottom face 42 of stator 2 to create a fluid seal while maintaining shape integrity when subjected to the torsional forces created by rotation of rotor 15. Examples of suitable materials include: high density graphites, silicon carbide and polymers. In a preferred embodiment, slipper seal 51 is comprised of Polymer Blend 45® (a blend of ultra high molecular weight polyethylene and teflon), from Performance Plastics (San-Ysidro, Calif.), which is more specifically a polytetrafluoroethylene based product that is preferred due to machining ease, durability characteristics and cost efficiency.

To ensure a leak-tight seal is created between slipper seal top face 53 and bottom face 42 of stator 2, the adjoining surfaces can be smoothed by lapping the surfaces. However, it has been ascertained that the surfaces need not be lapped if the appropriate materials are used and the appropriate axial forces are generated by the system of springs in the apparatus.

Figure 88:
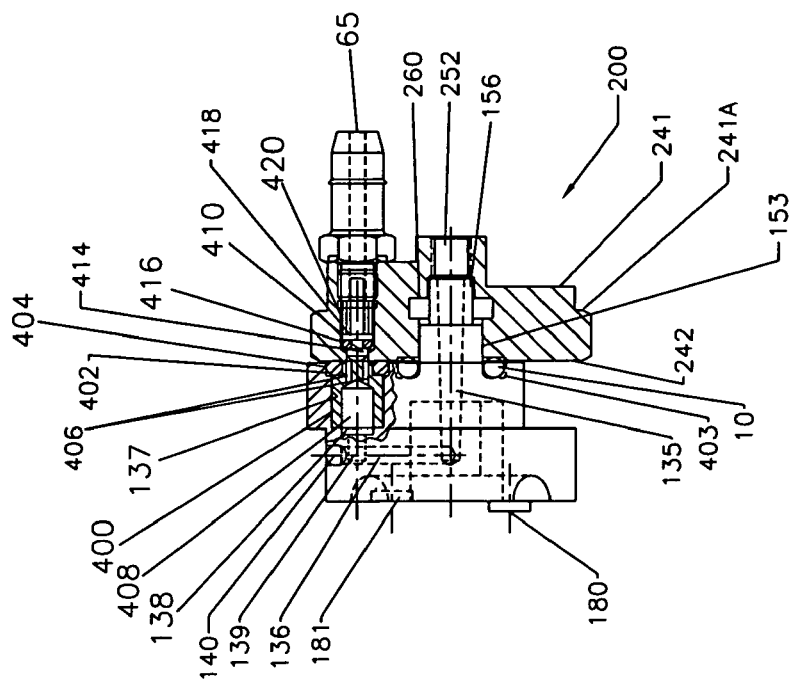
FIG. 88 is a side elevational view of a bottom rotor and stator sub-assembly according to one embodiment of the invention.

An alternative embodiment that substitutes a poppet assembly for a slipper seal assembly is shown in FIG. 88. In this embodiment, an actuator 400 is provided in fluid conveying bore 137. Actuator 400 can be secured to rotor 119 via force fit, adhesive or with a screw 425 (shown in FIG. 90) that is threaded into a bottom of actuator 400 through a bore formed from a top surface of bottom rotor/valve stem assembly 119 that is in communication with fluid conveying bore 137. Actuator 400 is secured to bottom rotor/valve stem assembly 119 before rotor/valve stem assembly 119 is joined to top rotor/valve stem assembly 118.

To ensure a tight seal between rotor/valve stem assembly 115 and stator 200, an actuator o-ring bore 402 is provided in concentric relation with conveying bore 137 to receive an actuator o-ring 404. A rotor o-ring channel 403 is provided about stator axle 153 to receive a rotor o-ring 405 which ensures a good seal between stator 200 and rotor/valve stem assembly 115. At least two actuator channels 406 are provided in a top portion of actuator 400 that open into and are in fluid communication with an actuator chamber 408 that is in turn, in fluid communication with fluid conveying counterbore 138.

Situated in each stator bore 246 is a poppet 410. A poppet top end 412 is preferably dome shaped and extends beyond a bottom surface 242 of stator 200. Formed proximal to poppet top end 412 is poppet o-ring channel 414 that is annular and sized to receive a poppet o-ring 416. Poppet 410 has a radially extending flange 418 that is situated adjacent to and forms a portion of poppet o-ring channel 416. A poppet compression spring 420 is set between a bottom end of barb 65 and poppet flange 418. Poppet compression spring 420 biases poppet 410 so that poppet o-ring 416 is forced against a shoulder 411 of stator bore 246 so that fluid flow between stator bore 246 and fluid conveying bore 137 is blocked when actuator 400 and poppet 410 are not in alignment. In a closed position, poppet top end 412 comes into contact with a bottom face of rotor/valve stem assembly 115.

When actuator 400 and poppet 410 come into contact and alignment via rotation of rotor/valve stem assembly 115, actuator 400 which has a top end that is preferably flush with the bottom surface of rotor/valve assembly 115, overcomes the force generated by the poppet spring 420 so that fluid communication between stator bore 246 and at least one actuator channel 406 is achieved. Preferably, at least two actuator channels 406 are provided in actuator 400 to ensure fluid communication in the event poppet 410 is radially displaced and blocks one of the actuator channels 406.

Figure 90:
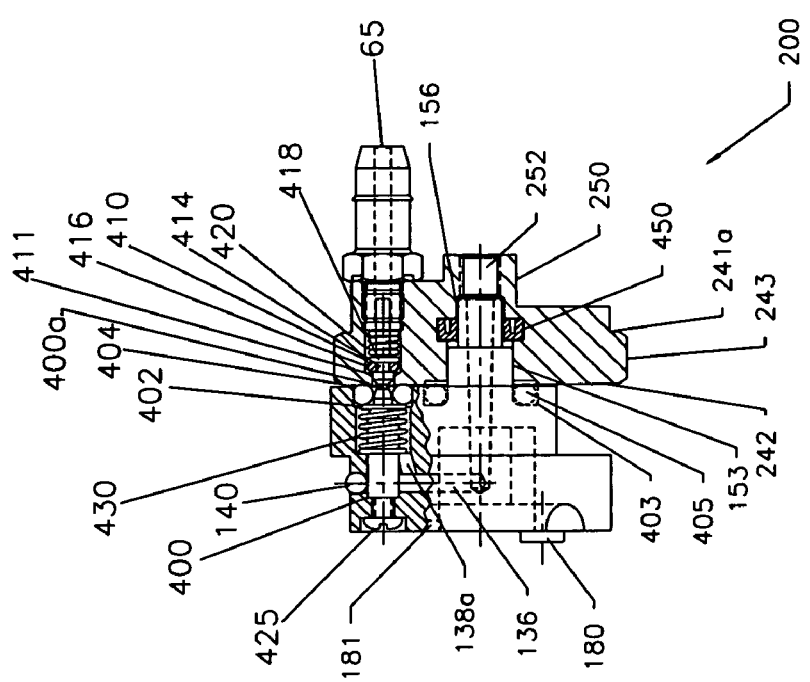
FIG. 90 is a side elevational view of a bottom rotor and stator sub-assembly according to one embodiment of the invention.

Another embodiment of the poppet form of seal is shown in FIG. 90. Actuator 400 is shown having a reduced diameter so that actuator 400 does not occlude fluid conveying bore 137. Provided about actuator 400 is actuator compression spring 430 that biases actuator o-ring 404 away from a distal tip 400*a* of actuator 400. Preferably distal tip 400*a* is tapered so that when actuator o-ring is biased toward distal tip 400*a*, fluid communication between stator bore 246 and fluid conveying channel 137 can be achieved about distal tip 400*a* when actuator 400 and poppet 410 are in alignment.

The presence of screw 425 occludes conveying aperture 139 and fluid conveying counterbore 138. To address the occlusion, auxiliary aperture 138*a* is provided to allow for fluid communication between transverse channel 136 and fluid conveying channel 137.

Figure 92:
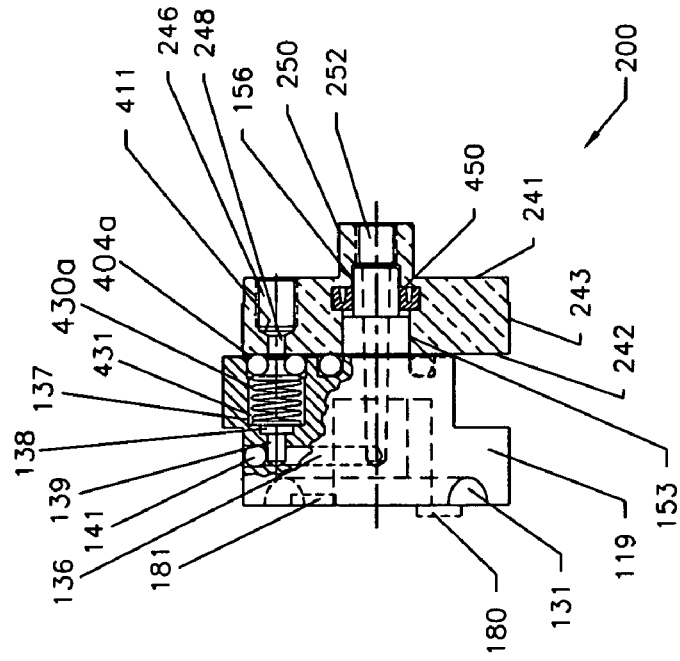
FIG. 92 is a side elevational view of a bottom rotor and stator sub-assembly according to one embodiment of the invention.

FIG. 92 shows a version of sealing the interfacing surfaces of rotor/valve stem assembly 115 and stator 200.

Figure 93:
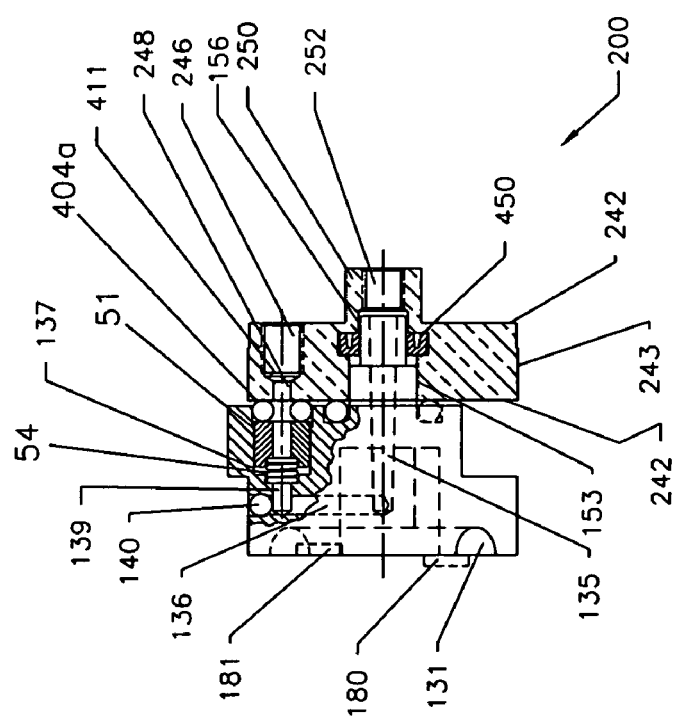
FIG. 93 is a side partial cutaway view of a bottom rotor and stator according to one embodiment of the invention.

Fluid conveying bore compression spring 430*a* contacts a bottom shoulder 431 formed between the junction of fluid conveying bore 137 and fluid conveying counterbore 138 and biases a conveying bore o-ring 404*a* against stator 200. This provides an adequate radial and axial seal when stator bore 246 is in alignment with fluid conveying bore 137. FIG. 93 shows a combination of a slipper seal and o-ring to seal the interfacing surfaces of rotor/valve stem assembly 115 and stator 200.

Figure 91:
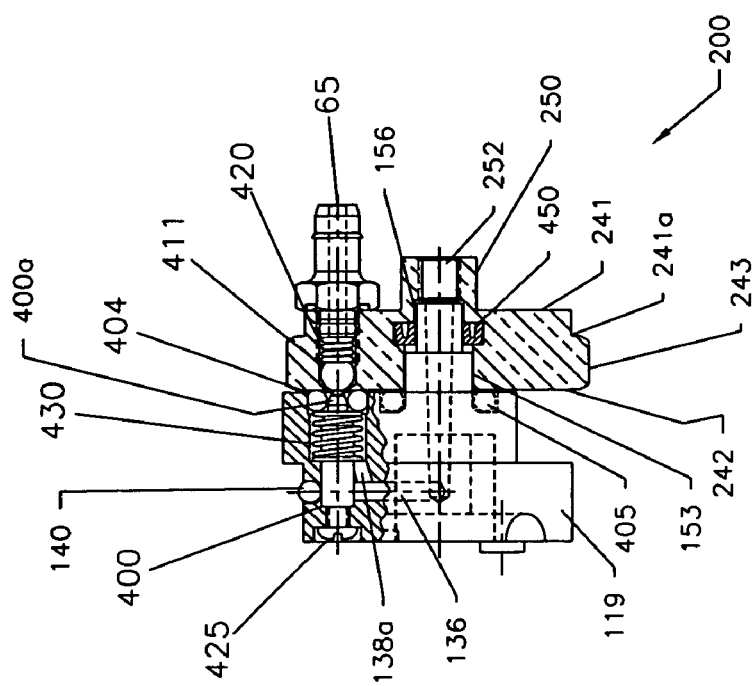
FIG. 91 is a side elevational view of a bottom rotor and stator sub-assembly according to one embodiment of the invention.

Turning to FIG. 91, a further poppet form of seal is shown where poppet 410 is replaced with poppet ball 415. When not in alignment with actuator 400, poppet ball 411 seats against shoulder 411 due to the bias produced by poppet spring 420.

Referring to FIGS. 39, 40, 56–57 and 89–93, a u-seal 450 is shown. U-seal 450 is preferably made of an elastomeric material that can withstand the application of forces along different axes. It has been found that u-seal 450 provides a good seal for the juncture of reduced neck 156 and stator 200, a junction that is subject to axial as well as rotational and torsional forces during operation of the multi-port valve assembly.

U-seal 450 has a flat bottom u-seal surface 452 that defines a central u-seal aperture 454. An inner annular u-seal wall 456 further defines u-seal aperture 454. An outer u-seal annular wall 458 is set at an angle relative to u-seal surface 452 so that outer u-seal wall 458 expands radially outwardly away from u-seal surface 452. Inner annular u-seal wall 456 expands radially inwardly away from u-seal surface 453 which results in outer u-seal wall 458 diverging from inner u-seal wall 456 to form an annular u-seal channel 460 that conforms to the shape of a trapezoid in cross-section. This configuration provides a seal that is capable of withstanding multi-directional forces. However, an o-ring can be substituted for u-seal 450 to provide a less effective but acceptable seal.

Referring now to FIGS. 13–18, valve stem 4 is shown. Valve stem 4 has a valve stem main body 72 that is sized to fit within large bore 10 of housing 1. It is important to the function of the apparatus that main body 72 can freely rotate within large bore 10.

Extending radially from main body 72 is valve stem top annular plate 13 which is sized to fit snugly within main annular wall 20 of housing 1 so that valve stem top annular plate 13 can rotate freely within housing 1. A bottom surface 73 of valve stem top annular plate 13 is chamfered to conform to annular chamfer 19 of housing 1. Bottom surface 73 is in frictional contact with ball bearings 17 which elevate valve stem 4 a fraction of an inch above annular chamfer 19 to allow free rotation of valve stem 4.

Valve stem 4 has a top annular plate 74 which is sized to fit within main rotor aperture 29 so that top annular plate 74 can rotate freely within main rotor aperture 29. Top annular plate 74 has portions which define detent housing channel 75. The combination of detent housing channel 75 and detent housing 60 lock rotor 15 and valve stem 4 together so that the two parts of the valve assembly rotate in unison.

Extending from a bottom end of valve stem main body 72 is attachment shaft 76 to which a variety of handles or knobs (not shown), can be attached to facilitate rotation of the rotor/valve stem assembly within housing 1. In one embodiment, as shown in FIGS. 14–18, attachment shaft 76 can have a shaft chamfer 77 and a key extension 78 to lock a handle or knob into rotational unison with valve stem 4.

Figure 27:
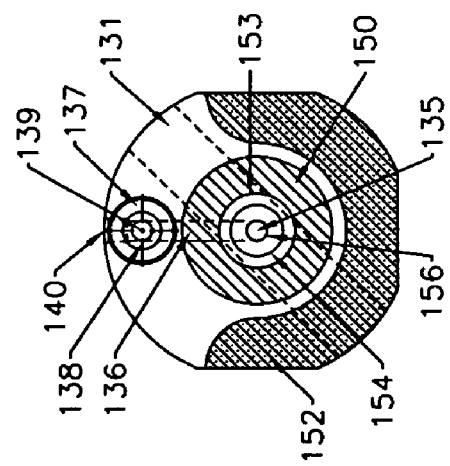
FIG. 27 is a bottom view of a rotor/valve assembly according to one embodiment of the invention.
Figure 26:
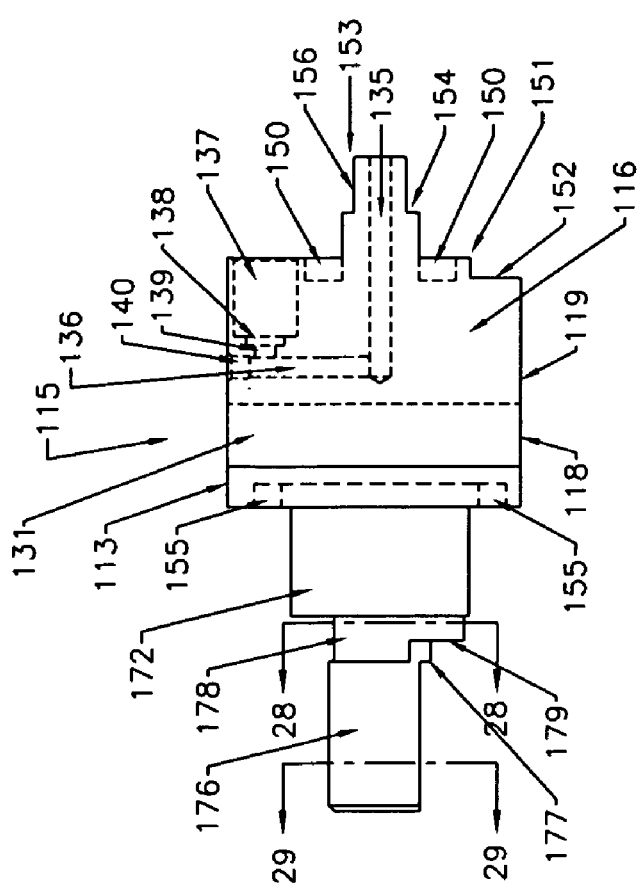
FIG. 26 is a side view of a rotor/valve assembly according to one embodiment of the invention.
Figure 30:
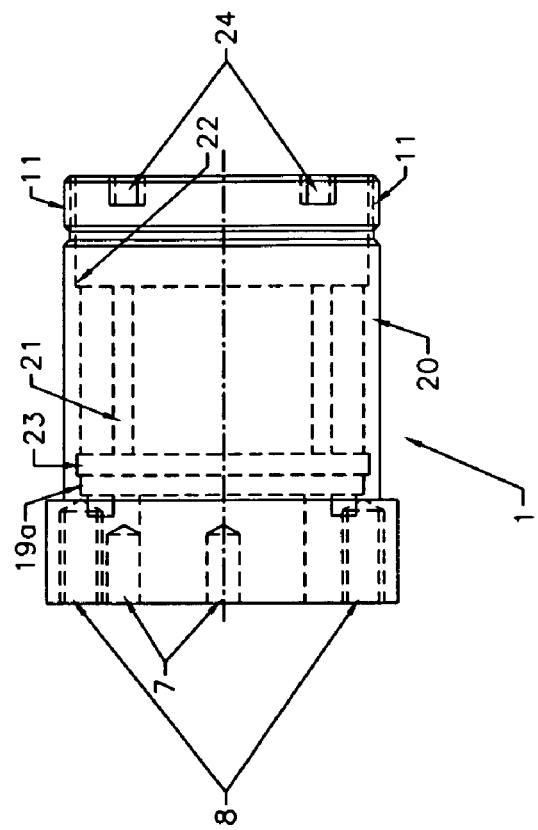
FIG. 30 is a side view of a housing according to one embodiment of the invention.
Figure 41:
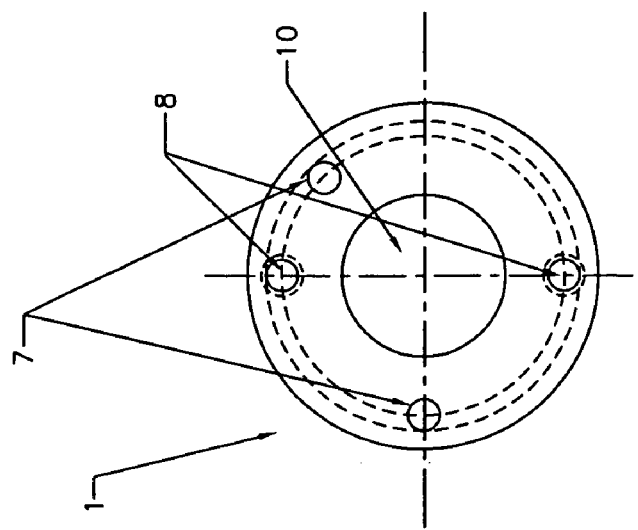
FIG. 41 is a bottom view of a housing according to one embodiment of the invention.

In a further embodiment, valve stem 4 and rotor 15 are combined into one component as shown in FIGS. 26 and 27. Rotor/valve stem assembly 115 has a main rotor/valve stem body 116 which has portions defining a detent housing aperture 131 for receiving detent housing 60. A first annular race 150 is formed on a top plate 151 which extends axially from a top surface 152 of rotor/valve stem assembly 115. Top plate 152 reduces the overall material needed for rotor/valve stem assembly 115.

Extending axially from top plate 151 is a preferably cylindrically shaped integral stator axle 153 that is sized to receive in rotational engagement, a corresponding aperture in a stator 200 described in more detail below. Extending axially from stator axle 153 is reduced neck portion 156, the junction of neck portion 156 and stator axle 153 forming axle shoulder 154. Formed and preferably radially centered within stator axle 153 and neck portion 156 is common central rotor fluid delivery bore 135.

Central fluid delivery bore 135 is in fluid communication with transverse channel 136 that extends radially from a preferably center point of main rotor/valve stem body 116 and opens on the exterior radial wall of main rotor/valve stem body 116. A plug 140 is secured via force fit, adhesive or other suitable method into the radial opening of transverse channel 136.

Extending downwardly from top plate 151 and radially outwardly from common central rotor fluid delivery bore 135 is fluid conveying bore 137. Extending downwardly and concentrically within the diameter of fluid conveying bore 137 is fluid conveying counterbore 138 which is sized to receive and engage a fluid receiving slipper seal as more fully described below.

Extending downwardly and concentrically within the diameter of fluid conveying counterbore 138 is fluid conveying aperture 139 which connects fluid conveying bore 137 with transverse channel 136. Fluid delivery bore 135 and fluid conveying bore 137 are in fluid communication via transverse channel 36.

Rotor/valve stem assembly 115 if formed from engineering grade plastic can be formed from two molded portions, a top rotor/valve stem assembly 118 and a bottom rotor/valve stem assembly 119. As shown in FIGS. 26, 28, 29, 68–72, 80, 87 and 89, top rotor/valve stem assembly 118 combines the features of valve stem 4 with some of the features of rotor 15.

Top rotor/valve stem assembly 118 has a valve stem main body 172 that is sized to fit within a large bore 110 of a housing 100 described in more detail below. It is important to the function of the apparatus that main body 172 can freely rotate within large bore 110.

Extending radially from valve stem main body 172 is rotor/valve stem assembly annular plate 113 which is sized to fit snugly within a main annular wall 120 of housing 100 so that rotor/valve stem assembly annular plate 113 can rotate freely within housing 100. A bottom surface 173 of annular plate 113 has an annular race 155 formed therein that receives ball bearings 17 which elevate rotor/valve stem assembly 115 a fraction of an inch above a bottom inner surface of housing 100 to allow free rotation of rotor/valve stem assembly 115.

Top rotor/valve stem assembly 118 has a post 174 which projects axially from a bottom surface of annular plate 113 and a cavity 174 formed in the bottom surface of annular plate 113. Post 175 and cavity 175 mate with a corresponding cavity and post, respectively, formed on bottom rotor/valve stem assembly 119 as described below. A main valve cavity 171 is formed in annular plate 113 and main body 172 when the assembly 115 is molded from plastic material. Main valve cavity 171 enables uniformity and proper heat dissipation when hot plastic is poured into a mold.

Extending from a top end of valve stem main body 172 is attachment shaft 176 to which a variety of handles or knobs (not shown), can be attached to facilitate rotation of the rotor/valve stem assembly within housing 100. In one embodiment, as shown in FIGS. 28, 29 and 37, attachment shaft 176 can have a shaft chamfer 177 and a key extension 178 to lock a handle or knob into rotational unison with rotor/valve stem assembly 115.

As shown in FIGS. 26, 27, 34–36, 73–77, 80 and 81, bottom rotor/valve stem assembly 119 has all the features previously described for rotor/valve stem assembly 115 with the following additional features. A top surface of bottom rotor/valve stem assembly 119 has a bottom post 180 that projects axially from the top surface and a bottom cavity 181 formed within the top surface. Bottom post 180 mates with cavity 175 and bottom cavity 181 mates with post 174 to ensure proper alignment of top rotor/valve stem assembly 118 to bottom rotor/valve stem assembly 119, each of which preferably form mating halves of detent channel 131. If made of plastic and molded, as shown in FIG. 34, bottom rotor/valve stem assembly 119 can be formed without transverse channel 136 which can later be formed by boring as is well known in the art. Similar to top rotor/valve stem assembly 118, if made by a molding process, optional main bottom cavity 182 can be formed in the mold (not shown), to ensure uniform cooling of molded bottom rotor/valve stem assembly 119.

As shown in FIGS. 52–54, 78, 79, 87, 87a, 89, 92 and 93, a stator 200 has, in a preferred embodiment, a central aperture and a plurality of peripheral apertures to allow for the selective delivery of fluids via fluid communication with rotor/valve stem assembly 115. Stator 200 has a stator top face 241 a stator bottom face 242, both of which, in a preferred embodiment, are annular in shape and have diameters that are less than the diameter of a stator side wall 243 which, in a preferred embodiment has a hexagonal shape. The hexagonal shape provides an interference fit with a portion of housing 100 to lock into place and center stator 200 relative to rotor/valve stem assembly 115.

The junction of stator top face 241 and stator side wall 243 form top shoulder 241a which centers stator 200 within an aperture provided in a bezel nut 300. Stator top face 241 is sized to fit within the diameter of bezel nut aperture 80. The combination of hexagonally shaped side wall 243, housing 100 having a hexagonally shaped cavity, top shoulder 241a and bezel nut aperture 380, secure the location of stator 2 relative to housing 100 and rotor/valve stem assembly 115 along the x, y and z axes.

Extending downwardly from stator top face 241 to a point short of stator bottom face 242 are a plurality of stator bores 246 which align with the fluid conveying bore 137 of rotor/valve stem assembly 115 when stator 200 is placed on rotor/valve stem assembly 115. Fluid communication between stator bores 246 and fluid conveying bore 137 is accomplished by stator apertures 248 that preferably have a diameter less than the diameter of stator bores 246 and are formed on the bottom face 242 oriented concentrically with stator bores 246. In a preferred embodiment, stator bores 246 having threading 247 to receive threaded barbs 65. In an alternate embodiment, barbs can be permanently fixed to stator bores 246 via methods such as brazing.

Extending axially from top face 241 is central stator post 250. Formed within central stator post 250 is stator delivery bore 252 the walls of which can have threads 254 to receive a central barb (not shown) having mating threads. Situated at a bottom end of stator delivery bore 250 is neck receiving bore 256 that is sized to receive neck 156 of rotor/valve stem assembly 115. Directly below neck receiving bore 258 is a u-seal receiving bore 260 that receives a u-seal 450 (described in more detail below). Directly below u-seal receiving bore 260 is stator axle receiving bore 262 that is sized to receive in rotational engagement, stator axle 153. Stator delivery bore 252, neck receiving bore 256, u-seal receiving bore 260 and stator axle receiving bore 262 are all in fluid communication.

In an alternative embodiment, stator 200 has a large bore 270 formed on bottom face 242 that eliminates apertures 248. Secured to large bore 270 is seal face 272. Seal face 272 provides a smooth, durable surface that interfaces with rotor/valve stem assembly 115. Seal face 272 can be made of any material such as Teflon® impregnated nylon or Delrin®.

Formed in seal face 272 are seal face apertures 274 that are positioned to be in alignment with and in communication with stator bores 246. Seal face apertures 274 reduce the cross-sectional area of the stator conveying apertures which prevents o-rings used in place of slipper seals in some embodiments of the invention from herniating into the cross-sectional area of the bores in stator 200. Preferably three seal face apertures 274 are used for each stator bore 246. However, two seal face apertures 274 have also reduced o-ring herniation.

In another alternative embodiment, a non-integral stator axle 600 can be used in place of integral stator axle 153. Axle 600 is designed to be threaded into the center of a top surface of rotor/valve stem assembly 115 at a bottom end and inserted into a bore formed in the center of bottom face 242 of stator 200. Axle 600 has a top axle bore 601 for receiving a glan nut 620.

Figure 49:
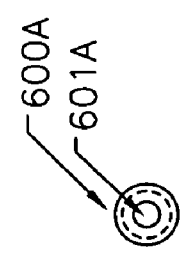
FIG. 49 is a top view of a barb according to one embodiment of the invention.
Figure 48:
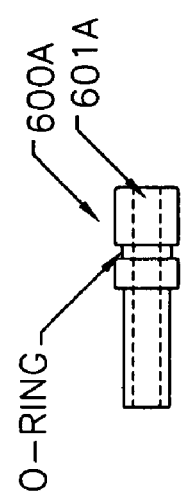
FIG. 48 is a side view of barb according to one embodiment of the invention.
Figure 51:
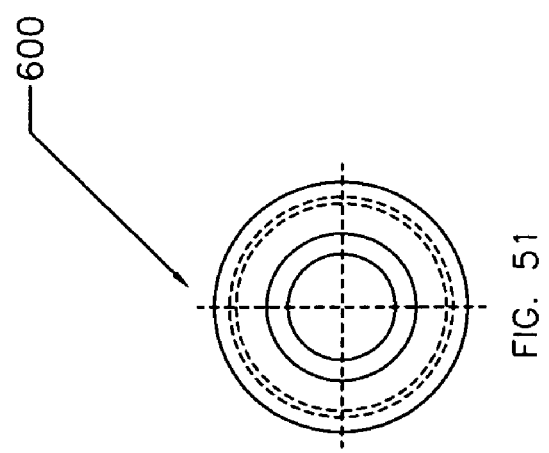
FIG. 51 is a side view of a stator axle according to one embodiment of the invention.
Figure 50:
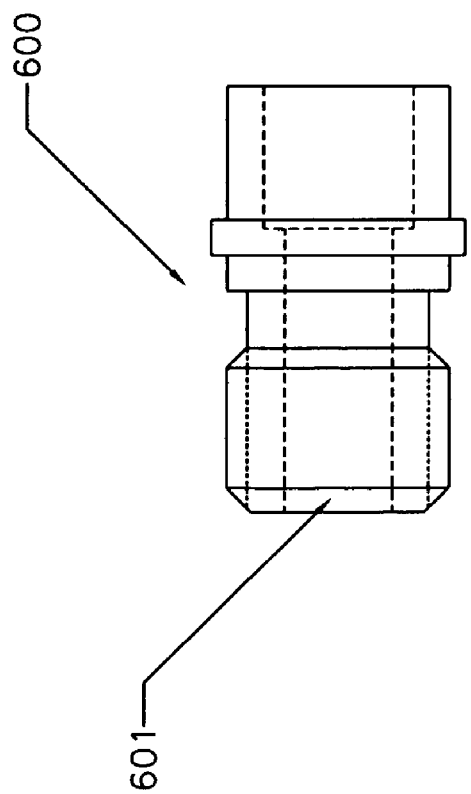
FIG. 50 is a tip view of a stator axle according to one embodiment of the invention.
Figure 79:
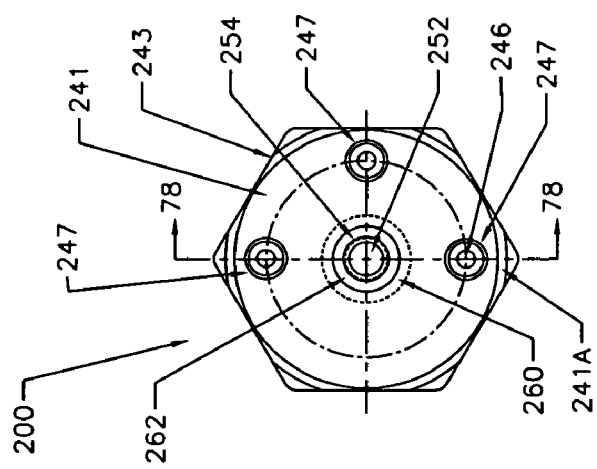
FIG. 79 is a top view of a stator according to one embodiment of the invention.
Figure 78:
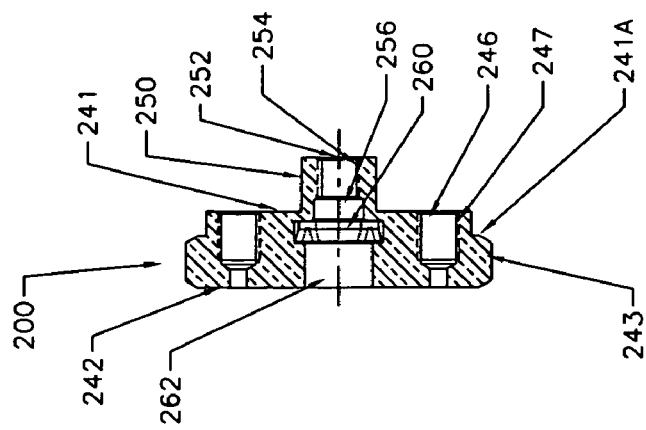
FIG. 78 is a sectional view of a stator according to one embodiment of the invention.
Figure 81:
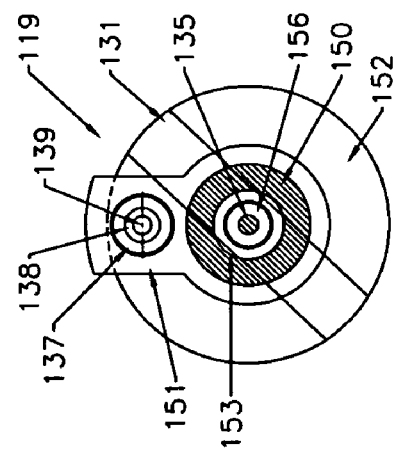
FIG. 81 is a top view of a valve stem/rotor assembly according to one embodiment of the invention.
Figure 80:
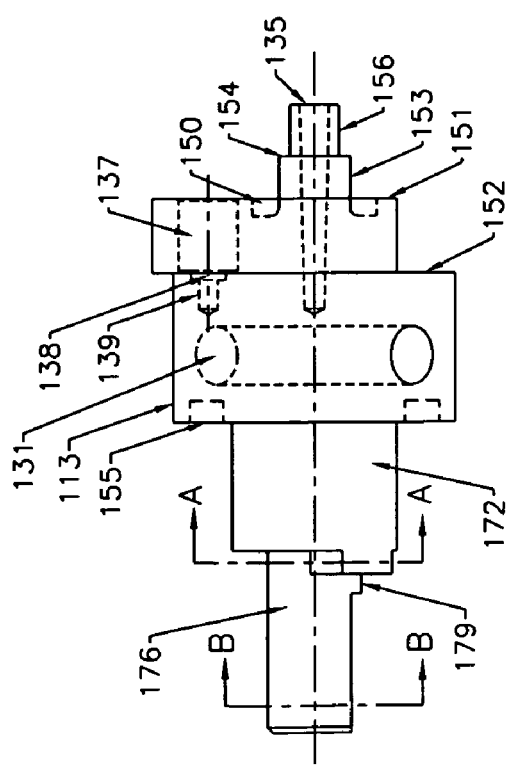
FIG. 80 is a side view of a valve stem/rotor assembly according to one embodiment of the invention.
Figure 86:
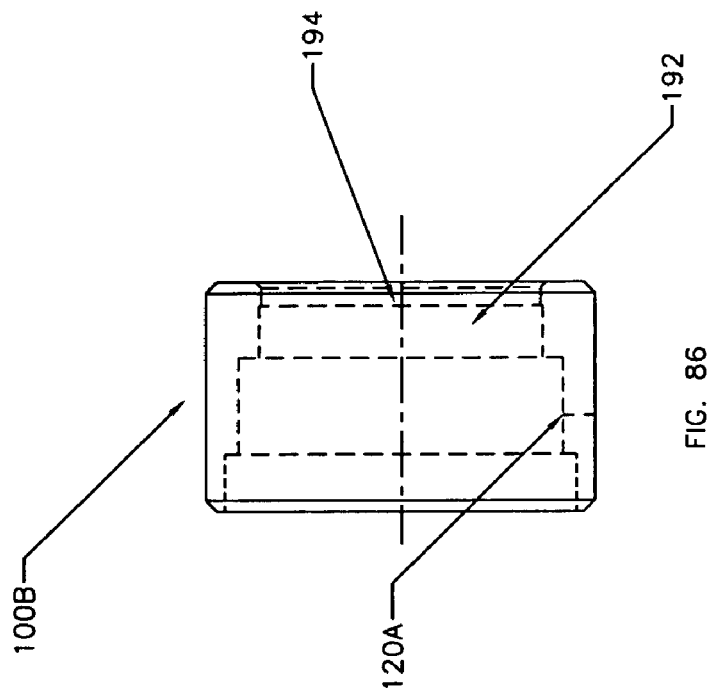
FIG. 86 is a side view of a bottom portion of a housing according to one embodiment of the invention.
Figure 85:
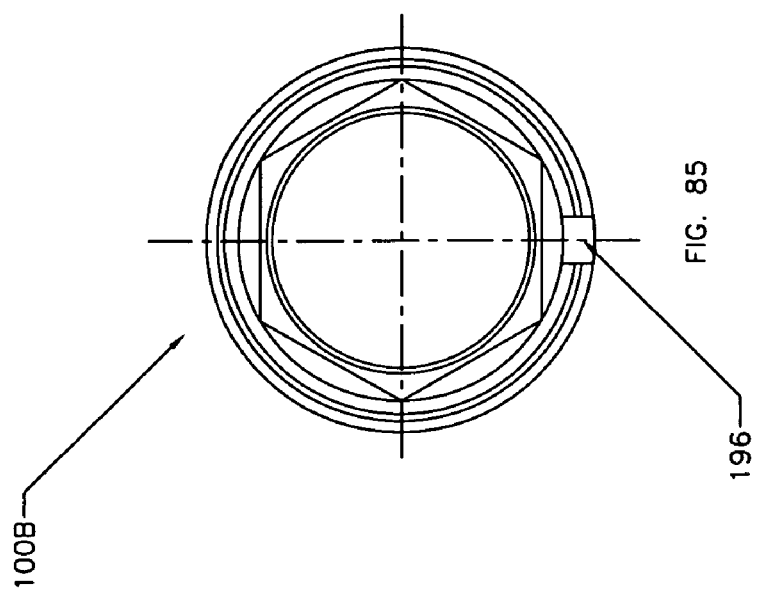
FIG. 85 is a top view of a bottom portion of a housing according to one embodiment of the invention.

Glan nut 620 is preferably threaded and screwed into a threaded bore 635 formed in the center of top face 241 of stator 200 to receive barb 65a shown in FIGS. 44 and 45. A glan nut slot 622 is provided on a top flange 621 of glan nut 620. A stepped glan nut through bore 625 is provided in glan nut 620 and sized to receive barb 65a as shown in FIG. 54. A u-seal 450 is provided between the interface of non-integral stator axle 600 and glan nut 620. Elastomeric or polymeric washers 627 can be placed between barb 65a and glan nut 620. An alternate embodiment of non-integral stator axle 600 is shown in FIGS. 48 and 49 as stator axle 600a that has a central through bore 601a that provides fluid communication between stator 200 and rotor/valve stem assembly 115.

Referring now to FIGS. 1, 2, 19 and 19a, bezel nut 3 is shown which has knurling 79 to ease torquing of bezel nut 3 onto housing 1. Torquing of bezel nut 3 can be used to create axial forces that oppose the axial preload generated by wave spring 14 and axial tension springs 54. This is accomplished by the dimensions of stator 2 and rotor 15 combined with the height and threading of bezel nut 3. With the right combination dimensions, the amount of torquing of bezel nut 3 onto housing 1 can be used to adjust and allow for the movement of rotor 15 within housing 1 within a suitable psi range that is preferably between 0 to 150. However, the primary functions of bezel nut 3 is to retain stator 2 and rotor 15 within housing 1 and to set the stack height of stator 2 and rotor 15 to establish a suitable axial preload in conjunction with wave spring 14.

Bezel nut 3 has portions which define a bezel nut aperture 80 which is sized to accept stator top face 41. Bezel nut 3 also has portions which define a bezel nut main aperture 81 which is sized to matingly engage housing 1 via bezel nut threading 82.

In an alternative embodiment, housing 1 and bezel nut 3 are replaced with a two-piece housing 100 that is preferably molded as shown in FIGS. 58–67 and 82–86. A top housing 100a like other embodiments has optional pin locator bores 107 in a top surface that can be provided to engage locator pins (not shown) projecting from a larger assembly to which the multi-port valve body is attached. Optional bore holes 108 can also be provided to accept mechanical fasteners (not shown). If threaded mechanical fasteners are used, bore holes 108 can be provided with threading extending axially along the portions of top housing 100a that define bore holes 108.

Situated in a main annular wall 120 of top housing 100a are a plurality of detent channels 121 which releasably arrest movement of rotor/valve stem assembly 115 within top housing 100a. The number and placement of detent channels 121 determine the number of positions and angular displacement of rotor/valve stem assembly 115 relative to stator 200. Molded slots 108a are provided to allow for uniform cooling of the material used to mold housing 100.

A main housing bore 119 is formed in top housing 100a to receive in rotational engagement, rotor/valve stem assembly 115. Formed on the top surface of top housing 100a is aperture 110 that is sized to receive the main valve stem body 172 portion of rotor/valve stem assembly 115 that project out of top housing 100a. A radially extended housing tab 109 is provided in on or in close proximity to a bottom end of top housing 100a to provide a means to align a bottom housing 100b described below.

As shown in FIGS. 58–62 and 85–86, bottom housing 100b replaces bezel nut 3. Bottom housing 100b has a top housing receiving bore for receiving the exterior wall of top housing 100a. A bottom end of top housing 100a is received in top housing receiving bore 190. Bottom housing 100b has a rotor bore 119a defined by bottom housing inner wall 120a that extends partially along the axial length of bottom housing 100b.

Bottom housing 100b has a stator side wall receiving bore 192 that is sized to receive in an interference fit, side wall 243 of stator 200. A stator receiving aperture 194 is formed on a bottom surface of bottom housing 100b to receive the top face 241 and acts as a stop with shoulder 142a.

A housing slot 196 is provided in the wall of bottom housing 100b to receive housing tab 109. The combination of housing slot 196 and housing tab 109 allow for the alignment of top housing 100a to bottom housing 100b and prevent relative rotational movement of the two components. Top housing 100a is preferably secured to bottom housing 100b with adhesive but can be configured to provide a force fit.

To assemble the multi-port valve, ball bearings 17 are introduced into annular housing chase 16 using the procedure previously described. Next, valve stem 4 is inserted into housing 1 from the top of housing 1 until seated on bearings 17. Wave spring 14 is set around top annular plate 74 of valve stem 4. Rotor 15 with detent housing 60 and detents 60a (ball bearings) pre-assembled in detent housing apertures 31 is placed within housing 1 so that main rotor aperture 29 engages top annular plate 74 via insertion of detent housing 60 into detent housing channel 75. Slipper seals 51, preassembled with axial torsion springs 54 and o-rings 59 are inserted into fluid delivery bore 33 and fluid conveying bore 37. Ball bearings 17 are then loaded into annular rotor chase 25. Next, stator 2 with, or without, delivery barb 61 and/or threaded barbs 65 pre-assembled, is inserted into the top of housing 1 until coming into contact with slipper seals 51 and ball bearings 17 which support stator 2. Lastly, bezel nut 3 is torqued onto housing 1 until an appropriate torque is achieved. An appropriate torque is achieved when valve stem 4 can be rotated from one detent stop to another.

To operate the unit, fluid hoses are attached to the barbs and a knob or handle is attached to the valve stem. Each detent channel is specifically positioned so that at least one conveying channel is connected via transverse fluid channel 36 to the delivery channel. The conveying channels are positioned so that any channel not in use can be depressurized rapidly after disengagement or engagement of one of the other conveying channels by the venting of pressure through the bottom of rotor 15 and out vent bore 12. The unique combination of the ball bearing support system with the slipper seals in a miniature multi-port valve provides a durable, almost air tight valve that can be easily changed from one fluid channel to another so that the fluid of choice can be delivered on demand. It has been found that the multi-port valve assembly exhibits superior sealing characteristics such that a bubble rate of 1 bubble per minute is experienced at 55 psi, i.e., "leak-tight" performance.

It is to be understood that the present invention is by no means limited to the particular constructions herein disclosed and/or shown in the drawings, but also comprises any modifications or equivalents within the scope of the claims.

Having thus described our invention, what we claim as new and desire to secure by United States Letters Patent is:

1. A multi-port valve comprising:
    a valve housing having a first housing aperture, second housing aperture, an annular housing chase situated about the second housing aperture;
    a valve stem having an annular flange sized to matingly engage the first housing aperture and a main valve stem body sized to matingly engage the second housing aperture such that the valve stem rotates freely within the housing;
    a rotor dimensioned to fit within the first housing aperture and having at least one rotor fluid receiving aperture and at least one rotor fluid delivery aperture wherein the rotor fluid receiving aperture is in fluid communication with the rotor fluid delivery aperture via a transverse channel;
    a stator having at least one stator fluid receiving aperture and at least one stator fluid delivery aperture wherein the stator is sized to matingly engage the first aperture of the housing; and, an actuator secured within the rotor fluid delivery aperture.

2. The multi-port valve of claim 1 further comprising a poppet in each of the at least one stator receiving aperture and the at least one stator fluid delivery aperture.

3. The multi-port valve of claim 2 wherein each poppet comprises an annular flange.

4. The multi-port valve of claim 3 further comprising a spring between the annular flange of each poppet and the stator.

5. The multi-port valve of claim 4 further comprising a poppet o-ring situated about each poppet.

6. The multi-port valve of claim 5 wherein the spring assembled to each poppet urges the poppet against the actuator when the actuator and poppet are aligned.

7. The multi-port fluid valve of claim 6 wherein the poppet is a poppet ball.

8. The multi-port fluid valve of claim 7 further comprising:
an actuator o-ring situated about the actuator proximate the junction between the rotor and the stator; and,
an actuator spring situated about the actuator wherein the actuator spring registers against and biases the actuator o-ring toward the stator to create a seal.

9. A multi-port valve comprising:
a valve housing having a first housing aperture, second housing aperture, an annular housing chase situated about the second housing aperture;
a valve stem having an annular flange sized to matingly engage the first housing aperture and a main valve stem body sized to matingly engage the second housing aperture such that the valve stem rotates freely within the housing;
a rotor dimensioned to fit within the first housing aperture and having at least one rotor fluid receiving aperture and at least one rotor fluid delivery aperture wherein the rotor fluid receiving aperture is in fluid communication with the rotor fluid delivery aperture via a transverse channel;
a stator having at least one stator fluid receiving aperture and at least one stator fluid delivery aperture wherein the stator is sized to matingly engage the first aperture of the housing;
an actuator secured within the rotor fluid delivery aperture, and,
a vent bore formed in a sidewall of the valve housing.

10. The multi-port fluid valve of claim 9 further comprising a wave spring positioned between the rotor and the valve stem.

11. The multi-port valve of claim 10 further comprising at least one detent channel formed on an inner surface of a sidewall of the valve housing.

12. The multi-port fluid valve of claim 11 further comprising a detent positioned in the rotor so as to engage the at least one detent channel.

13. The multi-port valve of claim 12 further comprising a detent spring positioned within the rotor so as to urge the detent against the detent channel.

14. The multi-port valve of claim 13 further comprising a bezel nut reversibly engaged to a top edge of the valve housing.

15. The multi-port fluid valve of claim 14 further comprising:
an annular chase formed within the valve housing; and,
a plurality of bearings positioned in the annular chase wherein the bearings register against the valve stem flange.

16. The multi-port fluid valve of claim 15 further comprising:
an annular rotor chase formed on the rotor; and,
a plurality of bearings positioned in the annular rotor chase wherein the bearings register against the stator.

17. The multi-port fluid valve of claim 10 further comprising a washer positioned adjacent to the wave spring.

18. The multi-port fluid valve of claim 17 wherein the wave spring, washer and valve stem flange are situated in planes occupied by the vent bore.

19. A multi-port valve comprising:
a valve housing having a first housing aperture, second housing aperture, an annular housing chase situated about the second housing aperture;
a valve stem having an annular flange sized to matingly engage the first housing aperture and a main valve stem body sized to matingly engage the second housing aperture such that the valve stem rotates freely within the housing;
a rotor dimensioned to fit within the first housing aperture and at least one rotor fluid receiving aperture and at least one rotor fluid delivery aperture situated within a rotor neck extending from a top surface of the rotor wherein the rotor fluid receiving aperture is in fluid communication with the rotor fluid delivery aperture via a transverse channel;
a stator having at least one stator fluid receiving aperture and at least one stator fluid delivery aperture formed within a stator post extending from a top surface of the stator, the stator post further comprising a bore dimensioned to receive the rotor neck, wherein the stator is sized to matingly engage the first aperture of the housing;
an actuator secured within the rotor fluid delivery aperture, and,
a vent bore formed in a sidewall of the valve housing.

20. The multi-port valve of claim 19 further comprising a u-seal positioned about the rotor neck and in registration with the walls of the stator post bore.

* * * * *